(12) United States Patent
Taft et al.

(10) Patent No.: US 10,039,905 B1
(45) Date of Patent: Aug. 7, 2018

(54) SYSTEMS FOR DEPLOYING AN EXPANDABLE CARDIAC SHUNT

(71) Applicant: Edwards Lifesciences Corporation, Irvine, CA (US)

(72) Inventors: Robert C. Taft, Irvine, CA (US); Emil Karapetian, Huntington Beach, CA (US); Cristobal R. Hernandez, Santa Ana, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 104 days.

(21) Appl. No.: 15/335,891

(22) Filed: Oct. 27, 2016

Related U.S. Application Data

(63) Continuation of application No. 15/287,369, filed on Oct. 6, 2016, now Pat. No. 9,789,294.

(60) Provisional application No. 62/262,052, filed on Dec. 2, 2015, provisional application No. 62/238,229, filed on Oct. 7, 2015.

(51) Int. Cl.
| | |
|---|---|
| *A61M 5/00* | (2006.01) |
| *A61M 27/00* | (2006.01) |
| *A61B 17/34* | (2006.01) |
| *A61B 90/00* | (2016.01) |

(52) U.S. Cl.
CPC ....... *A61M 27/002* (2013.01); *A61B 17/3403* (2013.01); *A61B 17/3468* (2013.01); *A61B 90/39* (2016.02); *A61B 2090/3966* (2016.02); *A61M 2210/125* (2013.01)

(58) Field of Classification Search
CPC ............ A61M 27/002; A61M 25/0194; A61M 25/04; A61M 25/06; A61M 25/1002; A61F 2/24; A61F 2/2409; A61F 2/2427; A61F 2/243
See application file for complete search history.

(56) References Cited

U.S. PATENT DOCUMENTS

| | | |
|---|---|---|
| 4,861,336 A | 8/1989 | Helzel |
| 5,287,861 A | 2/1994 | Wilk |
| (Continued) | | |

OTHER PUBLICATIONS

Emil Mantini, MD, et al., Title: Congenital Anomalies Involving the Coronary Sinus, Circulation, Journal of the American Heart Association, vol. XXXIII, Feb. 1966, pp. 317-327.

(Continued)

*Primary Examiner* — Philip R Wiest
(74) *Attorney, Agent, or Firm* — Guy Cumberbatch

(57) ABSTRACT

Disclosed are cardiac shunts and method of delivery, and in particular, to a shunt to reduce elevated left atrial pressure (LAP). The methods include forming a puncture hole between the left atrium and the coronary sinus, widening the puncture hole, and placing an expandable shunt within the widened puncture hole. A first catheter having a side-extending needle may be used to form a puncture into the left atrium. A second catheter extends along a guidewire and an expandable shunt with distal and proximal flanges is expelled therefrom into the puncture. The shunt defines a blood flow passage therethrough that permits shunting of blood from the left atrium to the coronary sinus when the LAP is elevated. The shunt is desirable formed of a super-elastic material and manipulated with control rods. The shunt defines a tilted flow tube that facilitates collapse into the catheter.

20 Claims, 25 Drawing Sheets

(56) References Cited

U.S. PATENT DOCUMENTS

| | | |
|---|---|---|
| 6,068,638 A | 5/2000 | Makower |
| 6,165,185 A | 12/2000 | Shennib et al. |
| 6,196,230 B1 | 3/2001 | Hall et al. |
| 6,251,116 B1 | 6/2001 | Shennib et al. |
| 6,302,875 B1 | 10/2001 | Makower et al. |
| 6,302,892 B1 | 10/2001 | Wilk |
| 6,387,119 B2 | 5/2002 | Wolf et al. |
| 6,468,303 B1 | 10/2002 | Amplatz et al. |
| 6,475,226 B1 | 11/2002 | Belef et al. |
| 6,562,066 B1 | 5/2003 | Martin |
| 6,616,675 B1 | 9/2003 | Evard et al. |
| 6,669,709 B1 | 12/2003 | Cohn et al. |
| 6,726,677 B1 | 4/2004 | Flaherty et al. |
| 6,776,785 B1 | 8/2004 | Yencho et al. |
| 6,808,498 B2 | 10/2004 | Laroya et al. |
| 6,893,413 B2 | 5/2005 | Martin |
| 6,926,690 B2 | 8/2005 | Renati |
| 7,037,329 B2 | 5/2006 | Martin |
| 7,294,115 B1 | 11/2007 | Wilk |
| D581,054 S | 11/2008 | Moore |
| D612,499 S | 3/2010 | Ondracek et al. |
| 7,729,738 B2 | 6/2010 | Flaherty et al. |
| 7,815,656 B2 | 10/2010 | Rust et al. |
| 7,828,814 B2 | 11/2010 | Brenneman et al. |
| 8,016,782 B2 | 9/2011 | Brenneman et al. |
| 8,070,708 B2 | 12/2011 | Rottenberg et al. |
| 8,088,171 B2 | 1/2012 | Brenneman |
| 8,187,217 B2 | 5/2012 | Renati et al. |
| D665,500 S | 8/2012 | Martin et al. |
| 8,235,933 B2 | 8/2012 | Keren et al. |
| 8,357,193 B2 | 1/2013 | Phan et al. |
| D679,015 S | 3/2013 | Nakaji |
| 8,641,724 B2 | 2/2014 | Brenneman et al. |
| D705,427 S | 5/2014 | Jagger et al. |
| 8,926,545 B2 | 1/2015 | Brenneman et al. |
| D723,166 S | 2/2015 | Igaki et al. |
| 8,951,276 B2 | 2/2015 | Kellerman et al. |
| 9,198,756 B2 | 12/2015 | Aklog et al. |
| 9,232,997 B2 * | 1/2016 | Sugimoto ............. A61L 31/022 |
| 9,345,485 B2 | 5/2016 | Dakin et al. |
| 2001/0034547 A1 | 10/2001 | Hall et al. |
| 2002/0169466 A1 | 11/2002 | Peterson et al. |
| 2005/0049675 A1 | 3/2005 | Wallace |
| 2005/0060041 A1 | 3/2005 | Phan et al. |
| 2005/0278013 A1 | 12/2005 | Rust et al. |
| 2007/0191872 A1 | 8/2007 | Stiger |
| 2012/0136426 A1 | 5/2012 | Phan et al. |
| 2012/0265296 A1 | 10/2012 | McNamara et al. |
| 2013/0178784 A1 | 7/2013 | McNamara et al. |
| 2014/0194971 A1 | 7/2014 | McNamara |
| 2015/0039084 A1 | 2/2015 | Levi et al. |
| 2015/0245908 A1* | 9/2015 | Nitzan ................. A61F 2/2415 623/2.13 |
| 2016/0296317 A1 | 10/2016 | Timmermans et al. |
| 2017/0106176 A1 | 4/2017 | Taft et al. |

OTHER PUBLICATIONS

P.K. Kong, et al., Title: Unroofed Coronary Sinus and Persistent Left Superior Vena Cava, The European Society of Cardiology, 2006, pp. 398-401.

Vandhana Scheller, et al., Title: Coronary Sinus to Left Atrial Communication, Case Report in Medicine, Ohio Heart and Vascular Center, vol. 2009, Article ID 790715, pp. 1-3.

Int'l. Search Report for PCT/US2016/056119, dated Jan. 24, 2017.

* cited by examiner

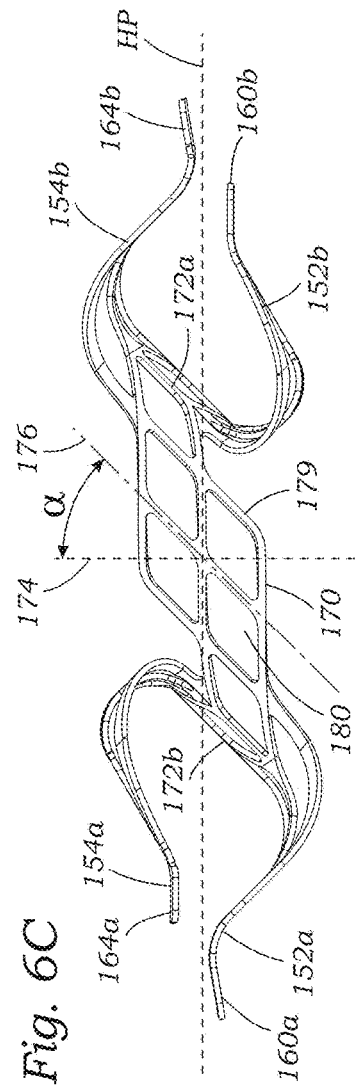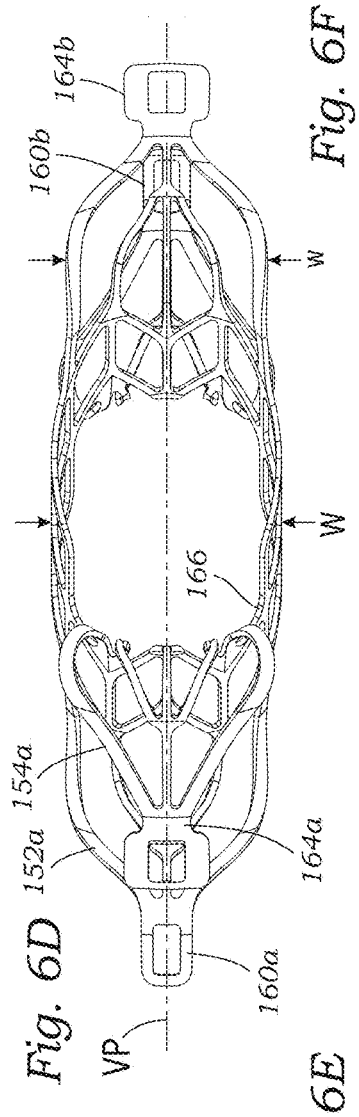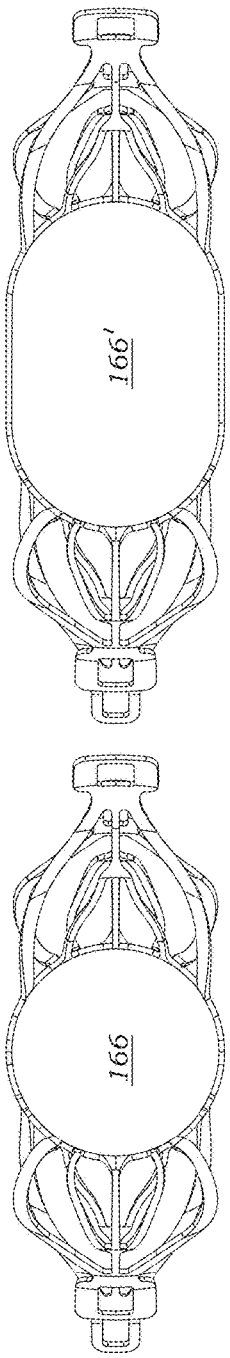

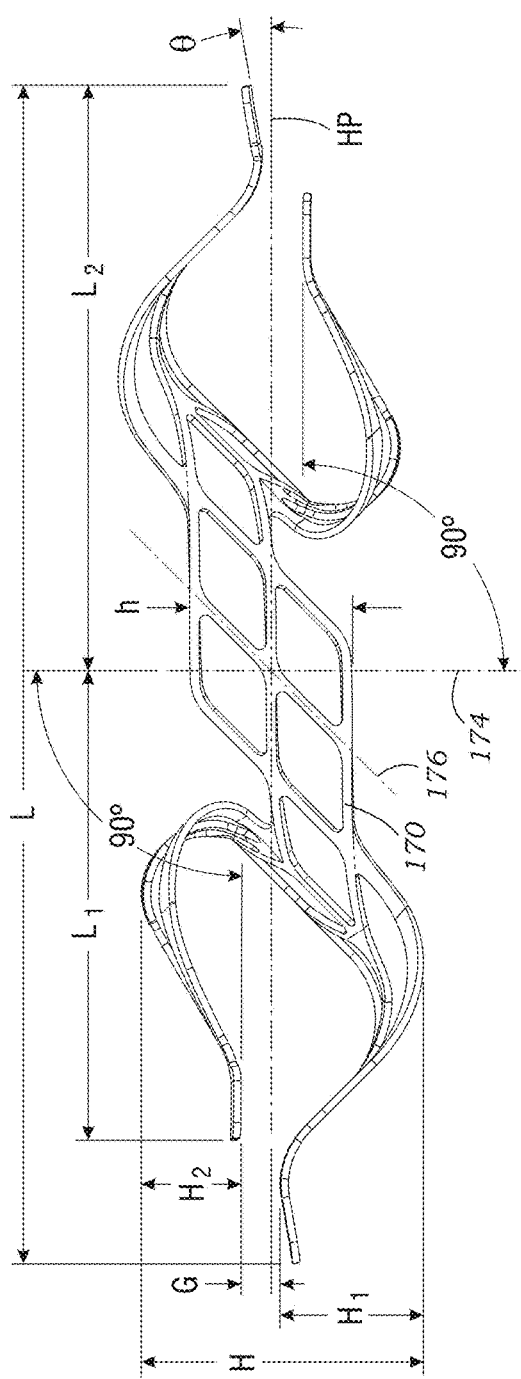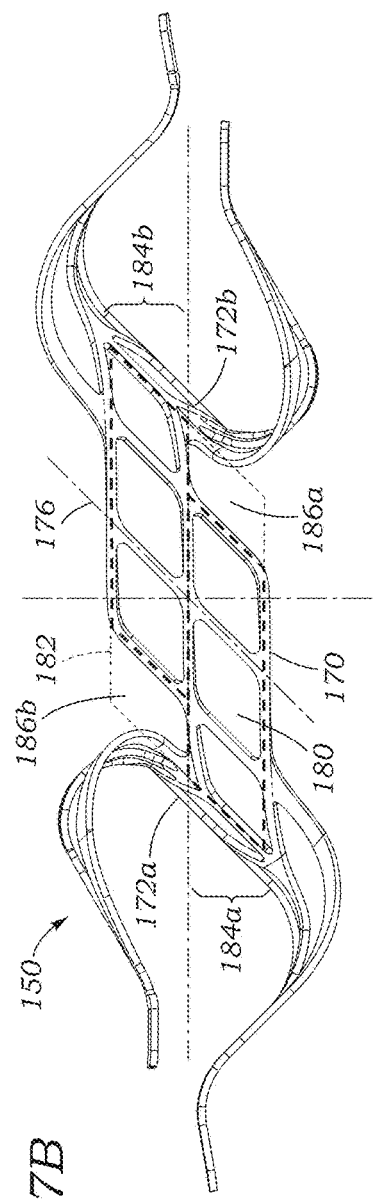
Fig. 7A
Fig. 7B

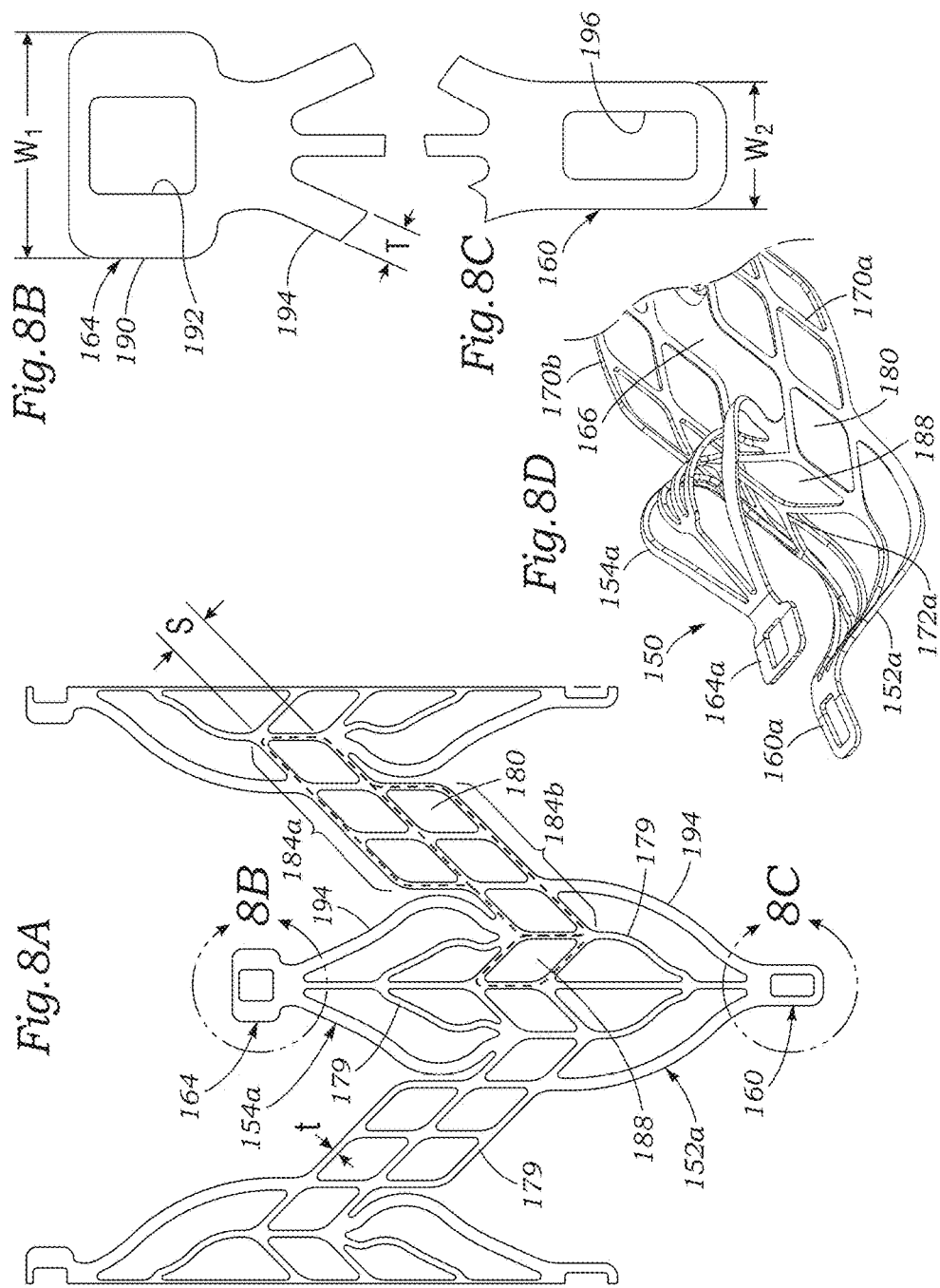

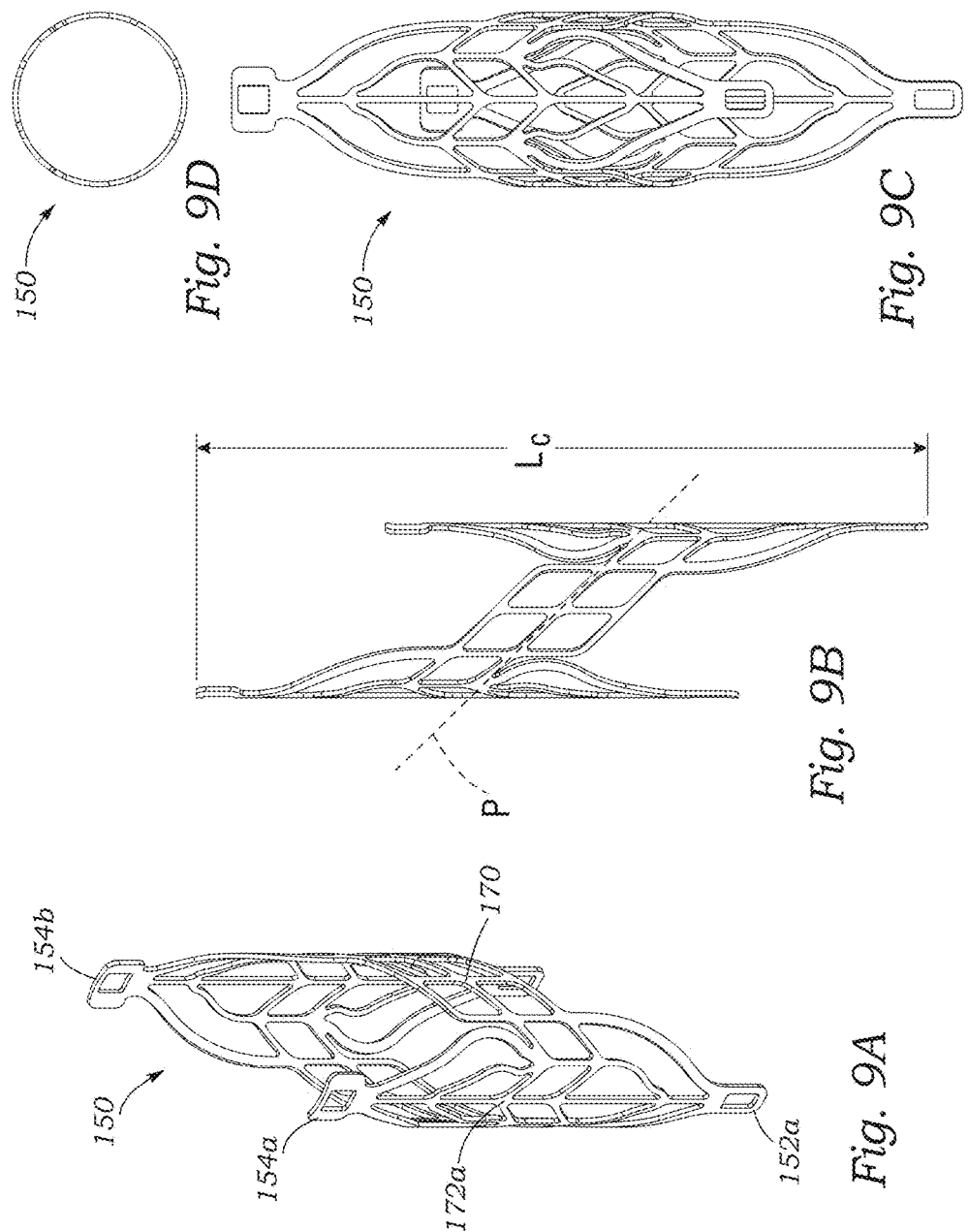

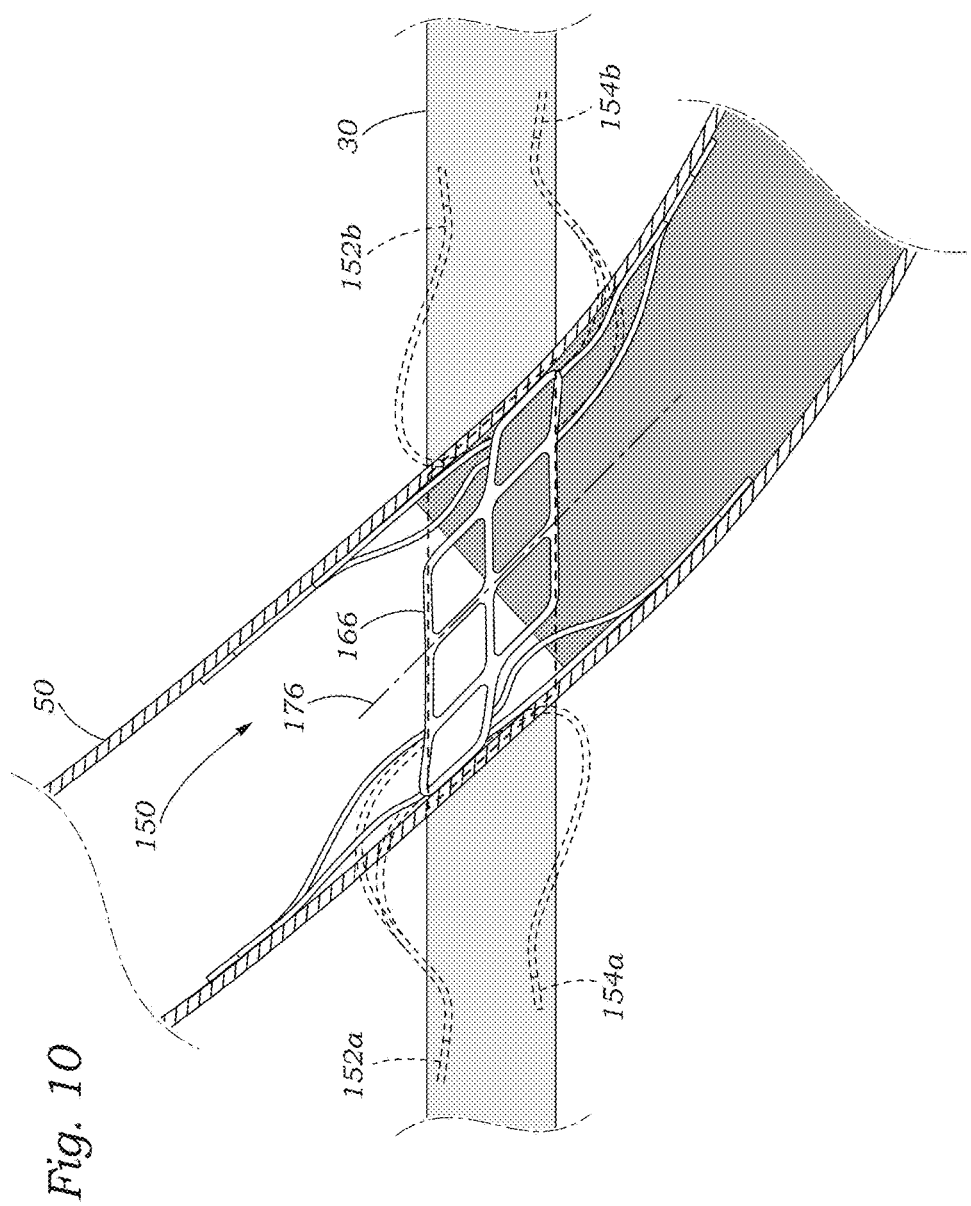

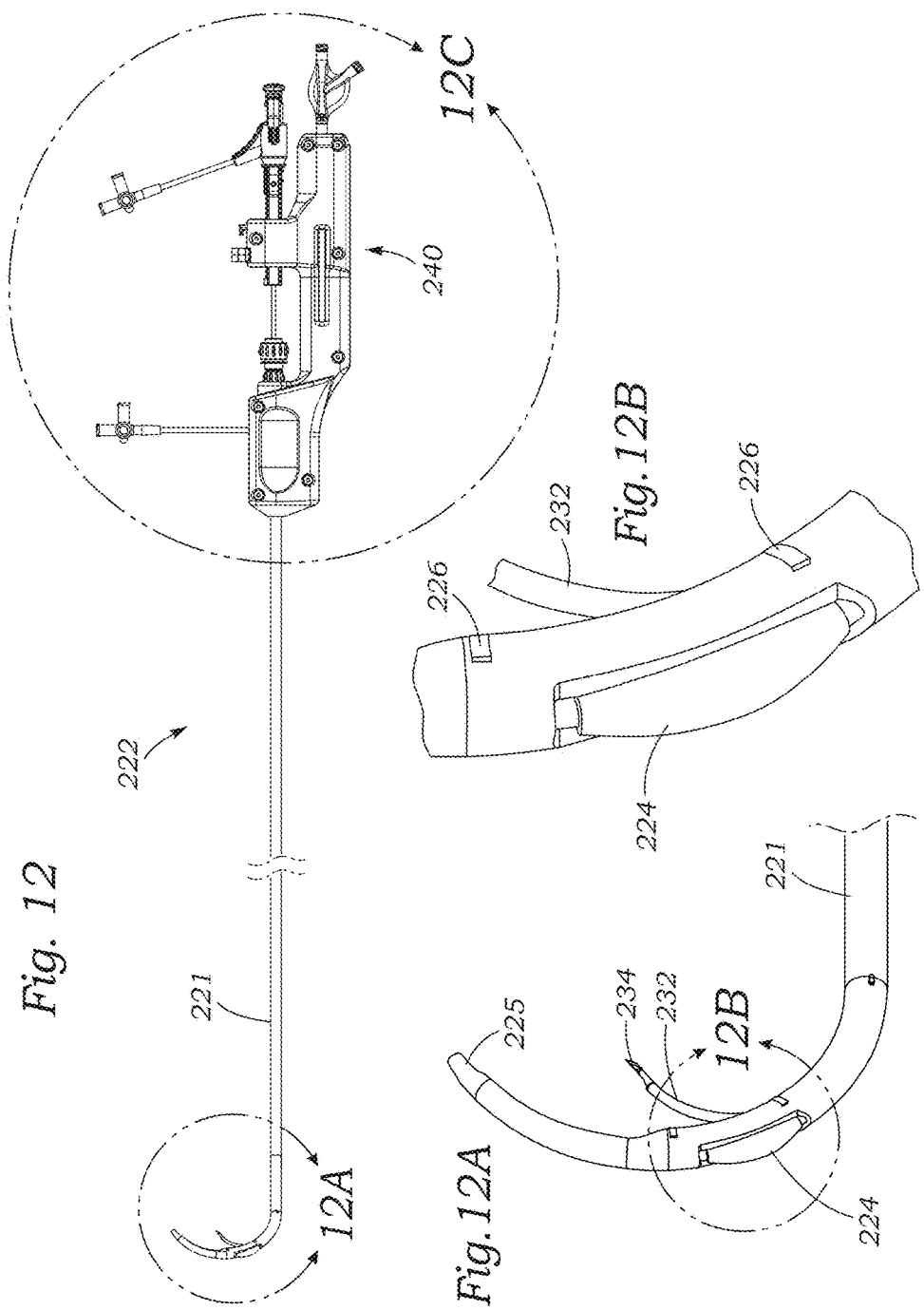

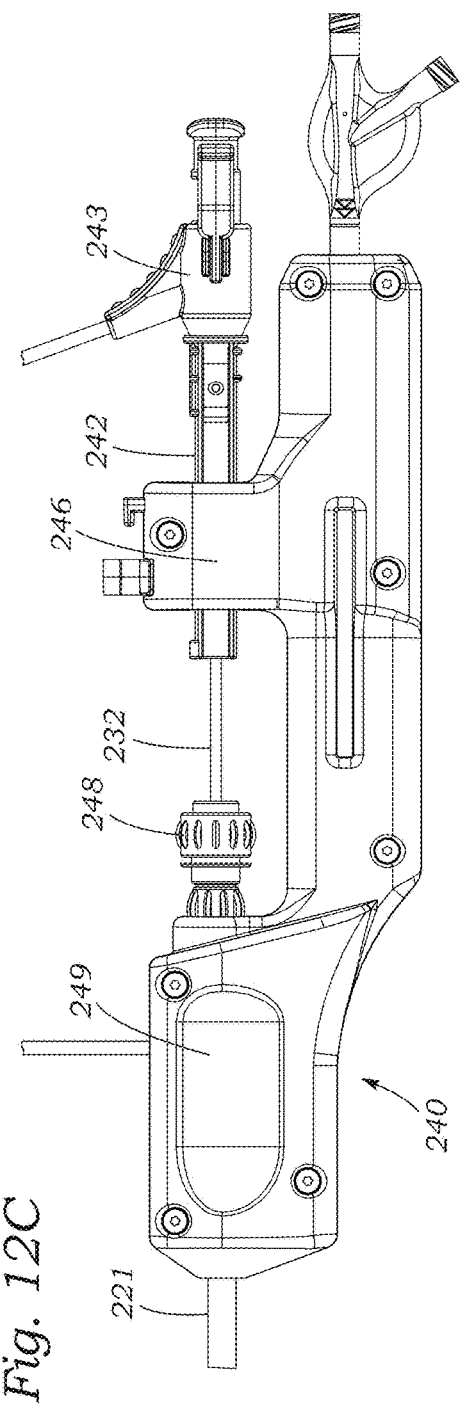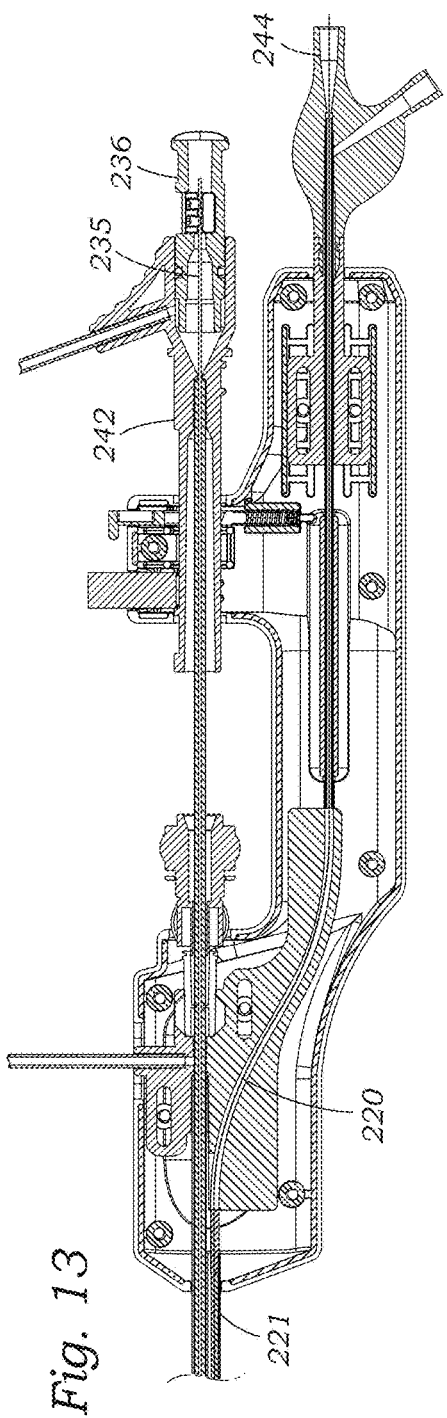

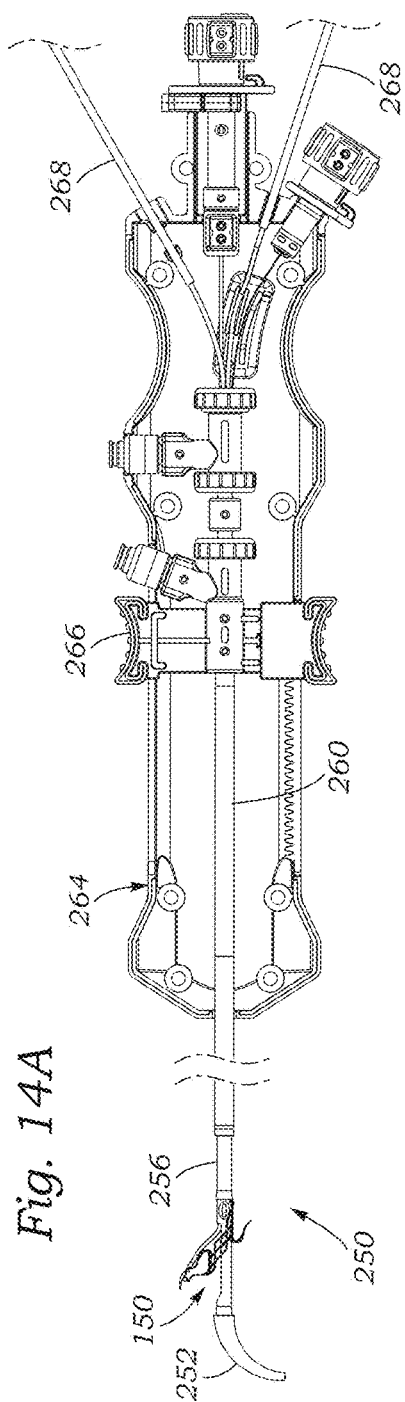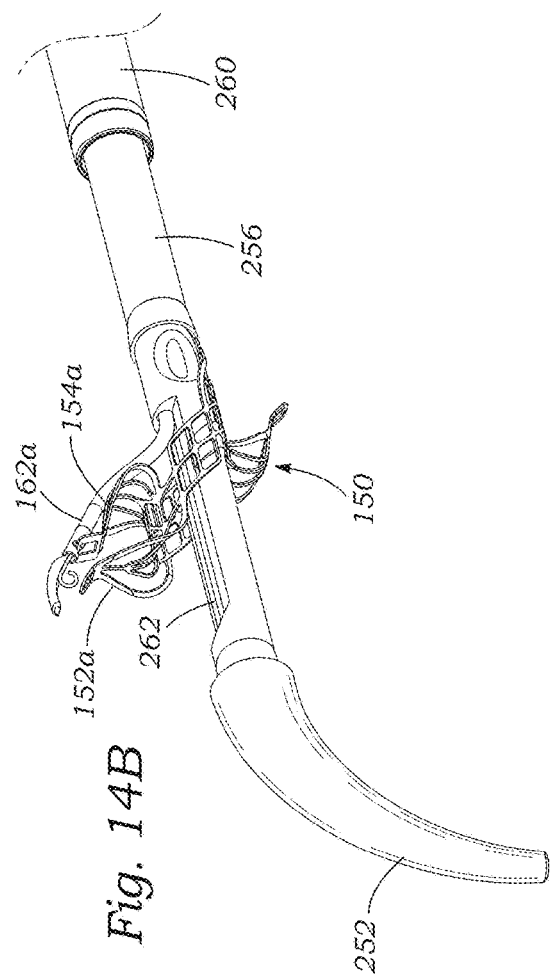

SYSTEMS FOR DEPLOYING AN EXPANDABLE CARDIAC SHUNT

RELATED APPLICATIONS

The present application is a continuation of U.S. Non Provisional application Ser. No. 15/287,369 filed Oct. 6, 2016 which claims priority under 35 U.S.C. 119 to both U.S. Provisional Application Ser. No. 62/262,052, filed Dec. 2, 2015 and U.S. Provisional Application Ser. No. 62/238,229, filed Oct. 7, 2015, the contents of which are expressly incorporated herein.

FIELD OF THE INVENTION

The present invention relates generally to cardiac shunts and systems and methods of delivery, and in particular, to a system for deploying a shunt to relieve left atrial pressure.

BACKGROUND OF THE INVENTION

In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary, and are each mounted in an annulus comprising dense fibrous rings attached either directly or indirectly to the atrial and ventricular muscle fibers. Each annulus defines a flow orifice. The four valves ensure that blood does not flow in the wrong direction during the cardiac cycle; that is, to ensure that the blood does not back flow through the valve. Blood flows from the venous system and right atrium through the tricuspid valve to the right ventricle, then from the right ventricle through the pulmonary valve to the pulmonary artery and the lungs. Oxygenated blood then flows through the mitral valve from the left atrium to the left ventricle, and finally from the left ventricle through the aortic valve to the aorta/arterial system.

Heart failure is a common and potentially lethal condition affecting humans, with sub-optimal clinical outcomes often resulting in symptoms, morbidity and/or mortality, despite maximal medical treatment. In particular, "diastolic heart failure" refers to the clinical syndrome of heart failure occurring in the context of preserved left ventricular systolic function (ejection fraction) and in the absence of major valvular disease. This condition is characterized by a stiff left ventricle with decreased compliance and impaired relaxation, which leads to increased end-diastolic pressure. Approximately one third of patients with heart failure have diastolic heart failure and there are very few, if any, proven effective treatments.

Symptoms of diastolic heart failure are due, at least in a large part, to an elevation in pressure in the left atrium. Elevated Left Atrial Pressure (LAP) is present in several abnormal heart conditions, including Heart Failure (HF). In addition to diastolic heart failure, a number of other medical conditions, including systolic dysfunction of the left ventricle and valve disease, can lead to elevated pressures in the left atrium. Both Heart Failure with Preserved Ejection Fraction (HFpEF) and Heart Failure with Reduced Ejection Fraction (HFrEF) can exhibit elevated LAP. It has been hypothesized that both subgroups of HF might benefit from a reduction in LAP, which in turn reduces the systolic preload on the left ventricle, Left Ventricular End Diastolic Pressure (LVEDP). It could also relieve pressure on the pulmonary circulation, reducing the risk of pulmonary edema, improving respiration and improving patient comfort.

Pulmonary hypertension (PH) is defined as a rise in mean pressure in the main pulmonary artery. PH may arise from many different causes, but, in all patients, has been shown to increase mortality rate. A deadly form of PH arises in the very small branches of the pulmonary arteries and is known as Pulmonary Arterial Hypertension (PAH). In PAH, the cells inside the small arteries multiply due to injury or disease, decreasing the area inside of the artery and thickening the arterial wall. As a result, these small pulmonary arteries narrow and stiffen, causing blood flow to become restricted and upstream pressures to rise. This increase in pressure in the main pulmonary artery is the common connection between all forms of PH regardless of underlying cause.

Despite previous attempts, there is a need for an improved way to reduce elevated pressure in the left atrium, as well as other susceptible heart chambers such as the pulmonary artery.

SUMMARY OF THE INVENTION

The present application discloses a method and several device embodiments that allow for elevated Left Atrial Pressure (LAP) to be reduced by shunting blood from the left atrium to the coronary sinus. By creating an opening between the left atrium and the coronary sinus, blood will flow from the higher pressure left atrium (usually >8 mmHg) to the lower pressure coronary sinus (usually <8 mmHg).

Using catheter-based instruments, the surgeon creates a puncture hole between the left atrium and the coronary sinus, and places an expandable shunt within the puncture hole. A first puncture catheter having a side-extending needle may be used to form a puncture into the left atrium. A second delivery catheter extends along a guidewire and an expandable shunt with distal and proximal flanges is expelled therefrom into the puncture. The shunt defines a blood flow passage therethrough that permits shunting of blood from the left atrium to the coronary sinus when the LAP is elevated. The shunt is desirable formed of a superelastic material and defines a tilted flow tube that facilitates collapse into the catheter.

The expandable blood flow shunts described herein are formed of an elastic material and configured to be inserted into a puncture wound in a tissue wall between two anatomical chambers and expand from a collapsed state to an expanded state to maintain a blood flow opening therebetween, the tissue wall defining a reference plane generally perpendicular to the opening.

In a first embodiment, the shunt in an expanded state includes a central flow tube defined by an opposed pair of lateral side walls formed by struts extending between an opposed pair of end walls formed by struts, the central flow tube defining a central axis therethrough angled from a reference axis extending perpendicular through the reference plane. Two distal flanges formed by struts each attach to a first axial end of the central flow tube, the distal flanges extending away from one another in opposite longitudinal directions generally parallel to the reference plane. Two proximal flanges formed by struts each attach to a second axial end of the central flow tube opposite the first end, the proximal flanges extending away from one another in opposite longitudinal directions generally parallel to the reference plane. The proximal flanges extend in the same directions as the distal flanges such that each proximal flange parallels one of the distal flanges to form a clamping pair of flanges with a gap therebetween sized to clamp onto the tissue wall.

In a second embodiment, the shunt in an expanded state includes a central flow tube defined by an opposed pair of lateral side walls formed by struts extending between an opposed pair of end walls formed by struts, the side walls and end walls together defining a tubular lattice and the central flow tube defining a central axis therethrough. Two distal flanges formed by struts connect to struts in the central flow tube at a first axial end thereof, the distal flanges extending away from one another in opposite longitudinal directions generally parallel to the reference plane, wherein there is one long and one short distal flange. Two proximal flanges formed by struts connect to struts in the central flow tube at a second axial end thereof opposite the first end, the proximal flanges extending away from one another in opposite longitudinal directions generally parallel to the reference plane. There is one long and one short proximal flange, the proximal flanges extending in the same directions as the distal flanges such that each proximal flange parallels one of the distal flanges to form a clamping pair of flanges with a gap therebetween sized to clamp onto the tissue wall. Further, the long distal flange and the short proximal flange form a clamping pair and the short distal flange and the long proximal flange form a clamping pair.

In a third embodiment, the shunt in an expanded state includes a central flow tube comprising an opposed pair of lateral side walls formed by struts that define open cells extending between an opposed pair of end walls formed by struts that define open cells. The side walls and end walls together define a tubular lattice and the central flow tube defines a central axis therethrough, wherein each side wall includes upper and lower rows of cells defined by the corresponding struts stacked along the central axis. Two distal flanges formed by struts connect to struts in the central flow tube at a first axial end thereof, the distal flanges extending away from one another in opposite longitudinal directions generally parallel to the reference plane. Two proximal flanges formed by struts connect to struts in the central flow tube at a second axial end thereof, the proximal flanges extending away from one another in opposite longitudinal directions generally parallel to the reference plane. The proximal flanges extend in the same directions as the distal flanges such that each proximal flange parallels one of the distal flanges to form a clamping pair of flanges with a gap therebetween sized to clamp onto the tissue wall. Additionally, the two rows of cells in each side wall stop short of the opposed end walls of the central flow tube to define spaces therebetween such that a first end wall directly connects only to the upper row of cells while a second end wall directly connects only with the lower row of cells.

In any of the shunt embodiment described herein, the struts of each of the proximal and distal flanges are desirably curved such that the flanges in each clamping pair of flanges initially curve away from each other and then converge toward each other at a terminal end thereof. Further, each clamping pair of flanges may include flanges of different lengths. Preferably, exemplary shunts have a maximum lateral width defined by the central flow tube. Additionally, the central flow tube of the shunts as viewed along their central axes are desirably circular. In a preferred embodiment, when the shunts transition from the collapsed to the expanded state a first flange in each clamping pair of flanges rotates outward more than 90° and a second flange in the same clamping pair of flanges rotates outward less than 90°. The struts of the lateral side walls may form connected parallelograms defining open cells therein. More particularly, each side wall may include upper and lower rows of parallelogram-shaped cells defined by the corresponding struts and stacked along the central axis, wherein the upper row connects to a first end wall only and the lower row connects to a second end wall only.

The present application further discloses a system for deploying any of the expandable shunts described above into a puncture wound in a tissue wall to maintain an opening therebetween, the tissue wall defining a reference plane. The system includes a delivery catheter having a proximal handle, an outer sheath surrounding an inner sheath. The shunt is mounted in a collapsed configuration on the inner sheath with the outer sheath surrounding and maintaining the shunt in a collapsed state with the proximal flanges oriented toward the handle. A pair of actuating rods extend from the handle distally through the inner sheath, each of which engages one of the proximal flanges of the shunt, the actuating rods being linearly slidable within the inner sheath. The system also has a puncture catheter with a proximal handle, an elongated flexible body having a distal tip, a guidewire lumen extending through the body from the handle to the distal tip, and a needle lumen extending through the body from the handle to a side port located near the distal tip. Finally, the system includes an elongated puncture sheath with a lumen and an elongated needle having a sharp tip sized to fit through the puncture sheath lumen such that the sharp tip projects therefrom. The puncture sheath is sized to pass through the needle lumen of the puncture catheter and project out of the side port to form a puncture in a tissue wall. The system may further include an expandable member sized to pass through the needle lumen and project out of the side port into the puncture, the expandable member being radially expandable to widen the puncture. The system may further include an expandable anchoring member located on the flexible body opposite the side port. A pair of radiopaque markers are preferably located distal and proximal to the expandable anchoring member on the side port side of the flexible body. The puncture catheter proximal handle may have an advancer for displacing the puncture sheath and a locking nut that fixes the puncture sheath relative to the handle.

An alternative system for deploying the expandable shunts described herein into a puncture wound in a tissue wall to maintain an opening therebetween is disclosed, the wall defining a reference plane. The system includes a delivery catheter having a proximal handle, an outer sheath surrounding an inner sheath. The shunt is mounted in a collapsed configuration on the inner sheath with the outer sheath surrounding and maintaining the shunt in a collapsed state with the proximal flanges oriented toward the handle. A pair of actuating rods extend from the handle distally through the inner sheath, each of which engages one of the proximal flanges of the shunt, the actuating rods being linearly slidable within the inner sheath. A puncture catheter has a proximal handle, an elongated flexible body having a distal tip, a guidewire lumen extending through the body from the handle to the distal tip, and a needle lumen extending through the body from the handle to a side port located near the distal tip. The puncture catheter further includes an expandable anchoring member located on the flexible body opposite the side port. Finally, a puncture sheath is sized to pass through the needle lumen and project out of the side port to form a puncture in a tissue wall. The elongated puncture sheath preferably has a lumen and an elongated needle having a sharp tip sized to fit through the puncture sheath lumen such that the sharp tip projects therefrom. The alternative system may further include an expandable member sized to pass through the needle lumen and project out of the side port into the puncture, the expandable member being radially expandable to widen the puncture. Further, a pair of radiopaque markers are preferably located distal and proximal to the expandable anchoring member on the side port side of the flexible body. The alternative system also may have an elongated puncture sheath having a lumen and an elongated needle having a sharp tip sized to fit through the puncture sheath lumen such that the sharp tip projects therefrom, the puncture sheath being sized to pass through the needle lumen of the puncture catheter and project out of the side port to form a puncture in a tissue wall. The puncture catheter proximal handle may have an advancer for displacing the puncture sheath and a locking nut that fixes the puncture sheath relative to the handle.

In either shunt deployment systems described above, the central flow tube of the shunt is preferably defined by an opposed pair of lateral side walls formed by struts extending between an opposed pair of end walls formed by struts, the central flow tube defining a central axis therethrough angled from a reference axis extending perpendicular through the reference plane. The shunt is desirably mounted in its collapsed configuration within a recess near a distal end of the inner sheath with the central axis therethrough coinciding with a longitudinal axis of the inner sheath at the recess.

The present application also contemplates a method of deploying any of the shunts described herein into a puncture wound in a tissue wall to maintain an opening therebetween, the wall defining a reference plane. The method includes the steps of:
- establishing access to a patient's vasculature;
- advancing a first guidewire through the vasculature, into the right atrium and into the coronary sinus;
- advancing a first catheter having a side-extending needle along the first guidewire until the side-extending needle is positioned within the coronary sinus adjacent the left atrium;
- expanding a stabilizing anchor from the first catheter into contact with the coronary sinus wall, the stabilizing anchor being located on the first catheter opposite a needle port in a side of the first catheter;
- forming a puncture hole in a wall between the left atrium and the coronary sinus by advancing the side-extending needle from the needle port in the first catheter;
- advancing a second guidewire through a lumen in the side-extending needle to remain extending into the left atrium;
- withdrawing the first catheter;
- advancing a second catheter along the second guidewire until a distal tip thereof is positioned through the puncture and within the left atrium, the second catheter carrying the shunt
- partially expelling the shunt from within the catheter such that the distal flanges expand on a distal side of the tissue wall;
- retracting the second catheter until the distal flanges contact the distal side of the wall;
- fully expelling the shunt from within the catheter by expelling the proximal flanges such that the proximal flanges expand on a proximal side of the tissue wall and the clamping pairs hold the shunt in place in the tissue wall so as to define a blood flow passage therethrough.

The method preferably also includes widening the puncture hole using an expandable member that projects from the needle port. The tissue wall is preferably located between the coronary sinus and the left atrium and placing the shunt in the tissue wall permits shunting of blood between the left atrium and coronary sinus.

A further understanding of the nature and advantages of the invention will become apparent by reference to the remaining portions of the specification and drawings.

BRIEF DESCRIPTION OF THE DRAWINGS

Features and advantages of the present invention will become appreciated as the same become better understood with reference to the specification, claims, and appended drawings wherein:

FIGS. 6A-6D are perspective, elevational, and plan views of the exemplary expandable shunt in an expanded configuration, FIG. 6E is a view looking through a central flow tube along an angle, and FIG. 6F is a view similar to FIG. 6E through an alternative shunt having an oval-shaped flow tube;

FIGS. 7A and 7B are elevational views of the exemplary expandable shunt illustrating certain dimensions and advantageous structural features;

FIGS. 8A-8D are flattened and partial perspective views of the exemplary expandable shunt highlighting certain other advantageous features;

FIGS. 9A-9D are perspective and orthogonal views of the exemplary expandable shunt in a collapsed configuration for delivery through an access sheath or catheter;

FIG. 10 is a schematic view of an access sheath passing through a tissue wall with the exemplary expandable shunt therein in a collapsed configuration, and showing in phantom the shunt as it would be expanded in contact with the tissue wall;

FIG. 12 is an elevational view of an exemplary puncture catheter having a side-extending needle used to create a puncture in a sidewall of a vessel, and FIGS. 12A-12C are enlarged views of elements thereof;

FIG. 13 is a vertical sectional view through a proximal handle of the puncture catheter of FIG. 12;

FIG. 14A is an elevational view of a shunt deployment catheter of the present application showing interior components of a proximal handle, and FIG. 14B is an enlarged view of a distal end of the shunt deployment catheter.

DETAILED DESCRIPTION OF THE PREFERRED EMBODIMENTS

The present application discloses methods and devices that allow for elevated Left Atrial Pressure (LAP) to be reduced by shunting blood from the left atrium to the coronary sinus. The primary method includes implanting a shunt defining an open pathway between the left atrium and the coronary sinus, although the method can be used to place a shunt between other cardiac chambers, such as between the pulmonary artery and right atrium. The shunt is expandable so as to be compressed, delivered via a low profile sheath or tube, and expelled so as to resume its expanded state. The method also includes utilizing a deployment catheter that first creates a puncture in the wall between the left atrium and the coronary sinus. Details of these methods, implants and deployment systems will be described below.

Figure 1:
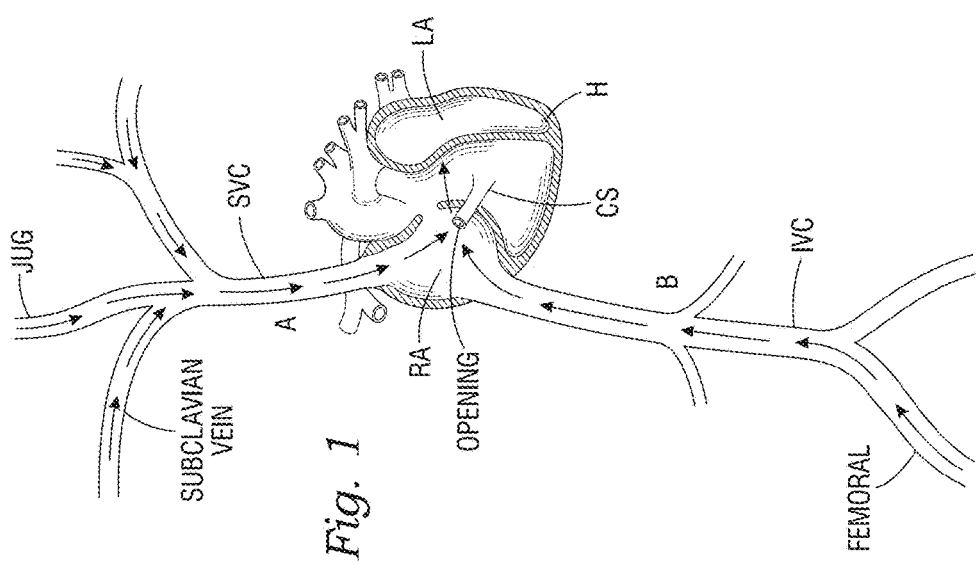
FIG. 1 is an overview of a heart illustrating how guidewires and catheters may be maneuvered in and around the heart to deploy expandable shunts of the present application.

FIG. 1 illustrates several access pathways for maneuvering guidewires and catheters in and around the heart to deploy expandable shunts of the present application. For instance, access may be from above via either the subclavian or jugular veins into the superior vena cava (SVC), right atrium (RA) and from there into the coronary sinus (CS). Alternatively, the access path may start in the femoral vein and through the inferior vena cava (IVC) into the heart. Other access routes may also be used, and each typically utilizes a percutaneous incision through which the guidewire and catheter are inserted into the vasculature, normally through a sealed introducer, and from there the physician controls the distal ends of the devices from outside the body.

Figure 2:
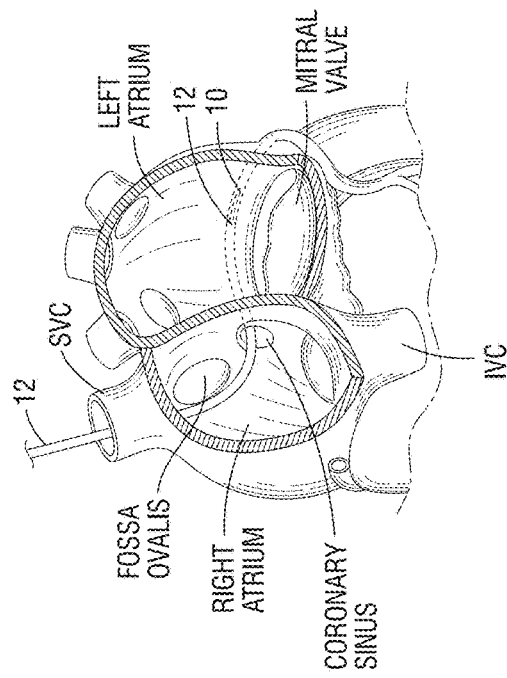
FIG. 2 shows a first catheter extending from the superior vena cava to the coronary sinus of the heart.

FIG. 2 depicts one approach method for deploying the expandable shunts described herein, wherein a guidewire 10 is introduced through the subclavian or jugular vein, through the superior vena cava and into the coronary sinus. Once the guidewire provides a path, an introducer sheath (not shown) may be routed along the guidewire and into the patient's vasculature, typically with the use of a dilator. FIG. 2 shows a deployment catheter 12 extending from the superior vena cava to the coronary sinus of the heart, the deployment catheter 12 having been passed through the introducer sheath which provides a hemostatic valve to prevent blood loss.

In one embodiment, the deployment catheter 12 may be about 30 cm long, and the guidewire 10 may be somewhat longer for ease of use. In some embodiments, the deployment catheter may function to form and prepare an opening in the wall of the left atrium, and a separate placement or delivery catheter will be used for delivery of an expandable shunt. In other embodiments, the deployment catheter may be used as the both the puncture preparation and shunt placement catheter with full functionality. In the present application, the terms "deployment catheter" or "delivery catheter" will be used to represent a catheter or introducer with one or both of these functions.

Since the coronary sinus is largely contiguous around the left atrium, there are a variety of possible acceptable placements for the stent. The site selected for placement of the stent, may be made in an area where the tissue of the particular patient is less thick or less dense, as determined beforehand by non-invasive diagnostic means, such as a CT scan or radiographic technique, such as fluoroscopy or intravascular coronary echo (IVUS).

Figure 3A:
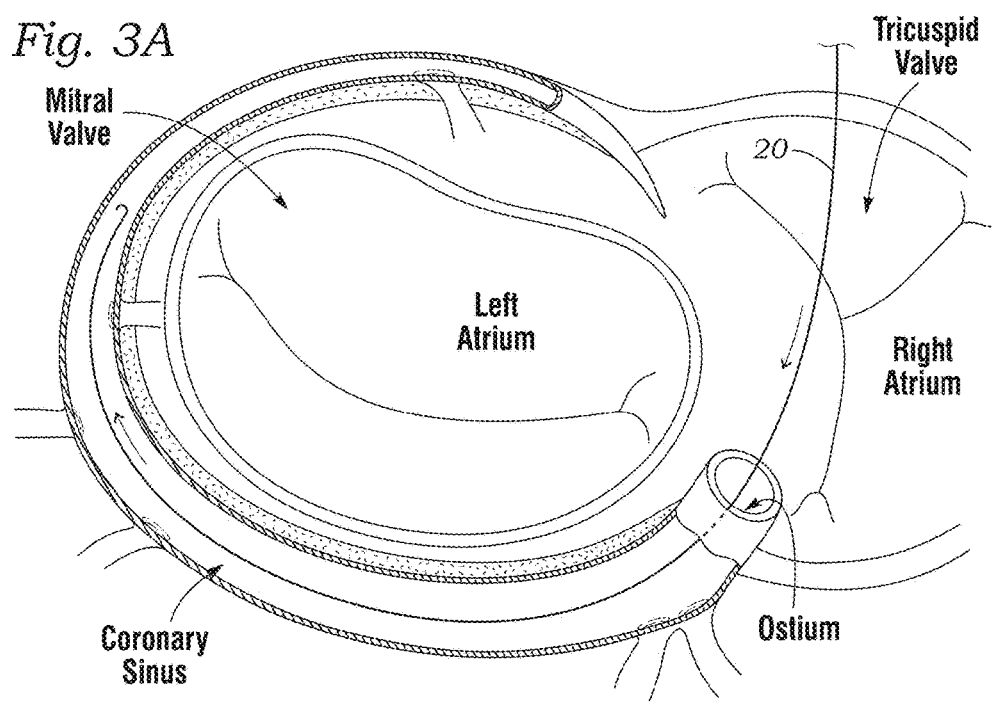
FIGS. 3A-3V are schematic views of steps in making a puncture hole through a wall of the coronary sinus and placement of a shunt between the coronary sinus and left atrium, as seen looking down on a section of the heart with the posterior aspect down.
Figure 3B:
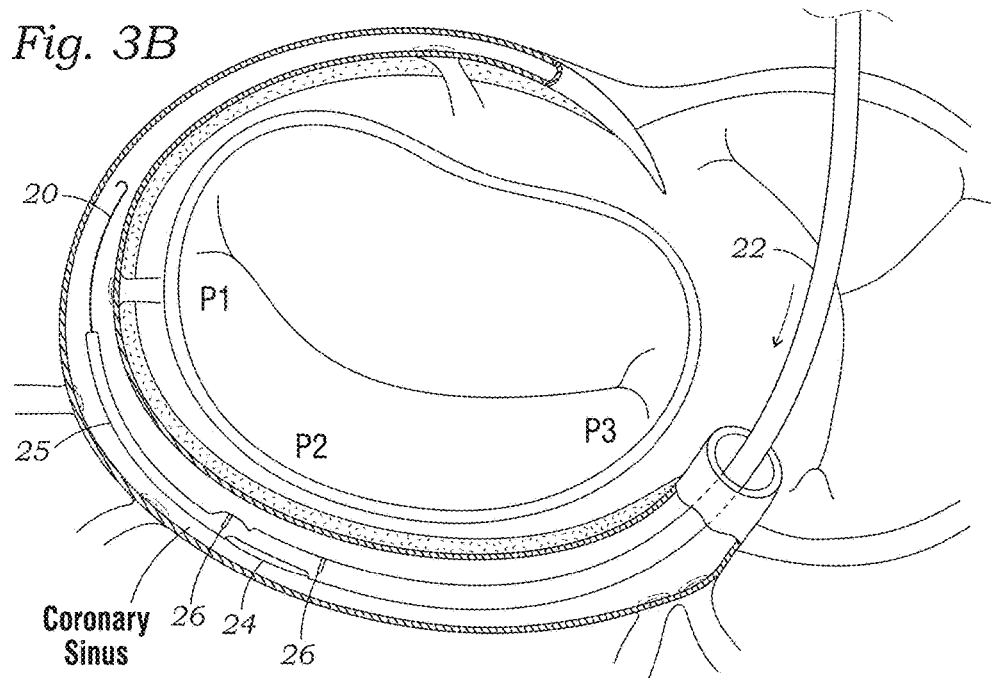
Figure 3C:
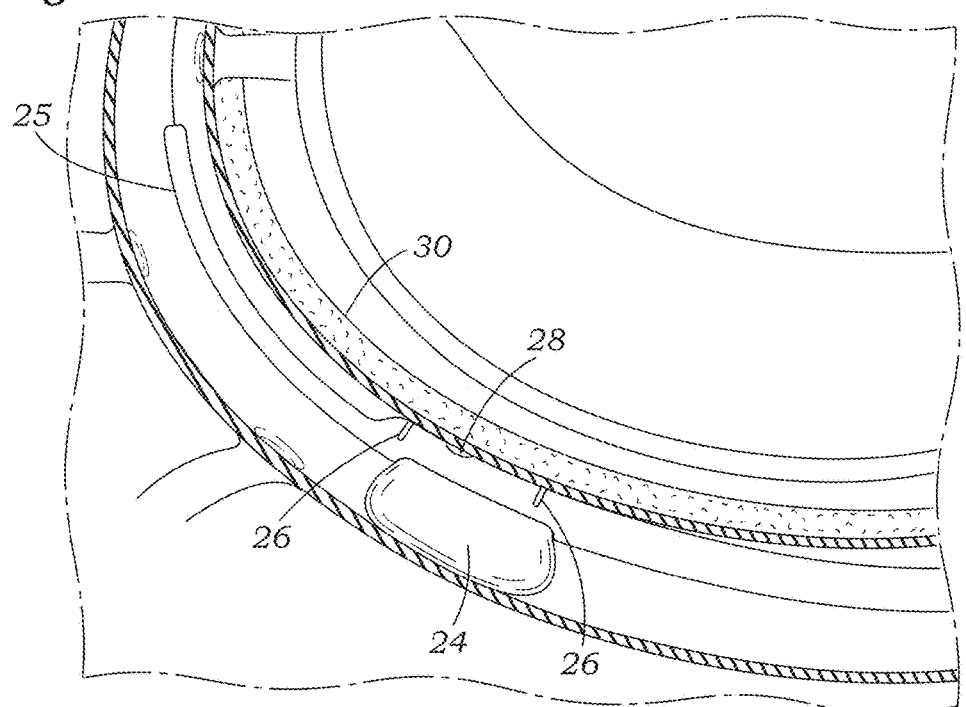
Figure 3D:
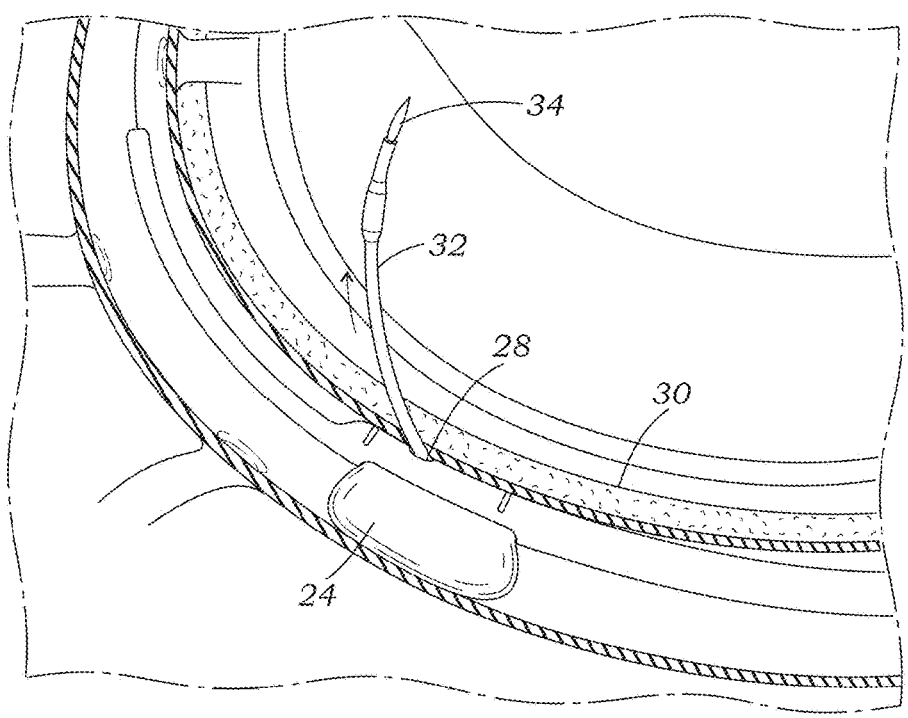
Figure 3E:
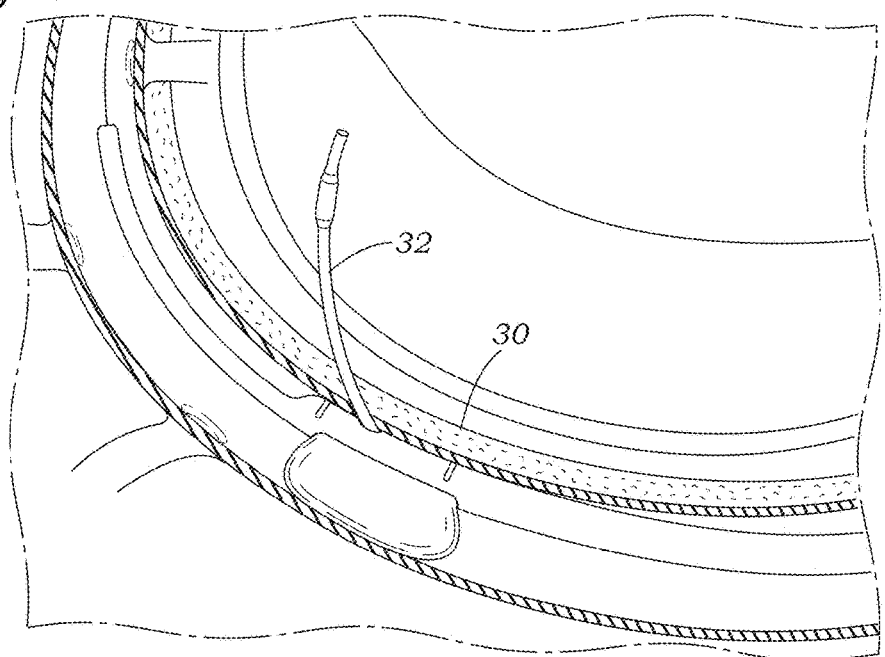
Figure 3F:
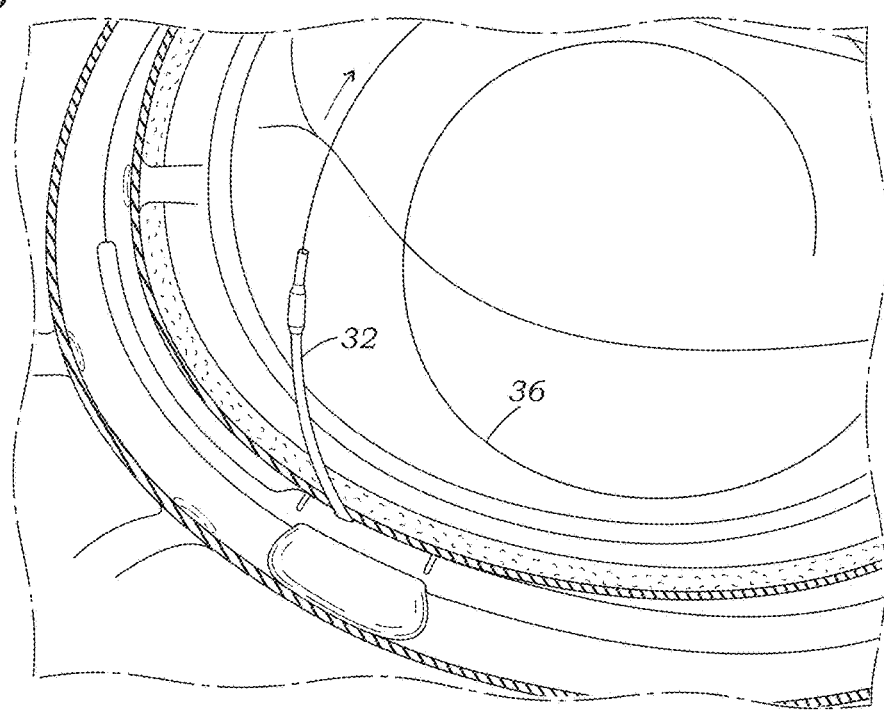
Figure 3G:
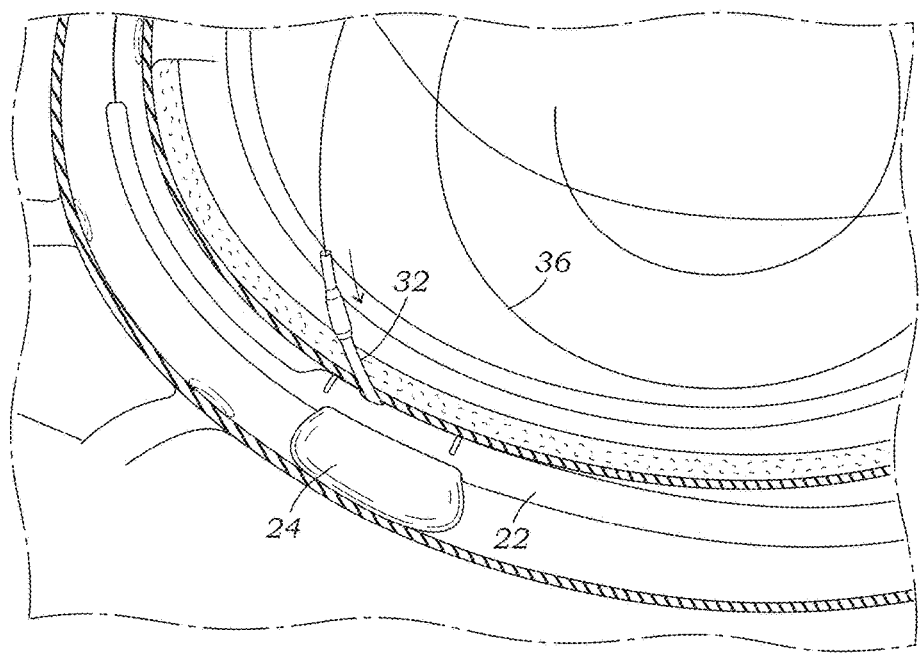
Figure 3H:
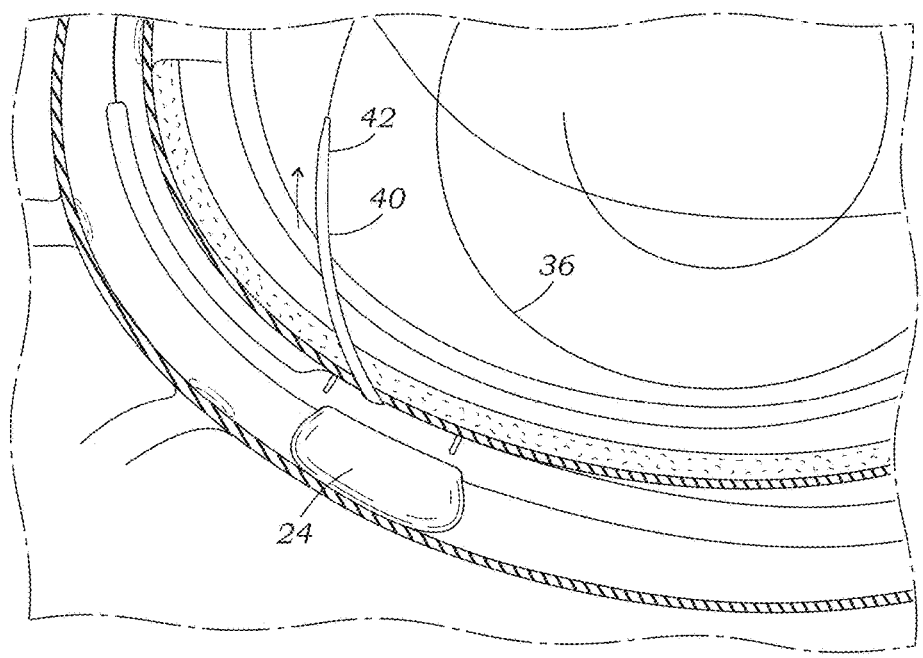
Figure 3I:
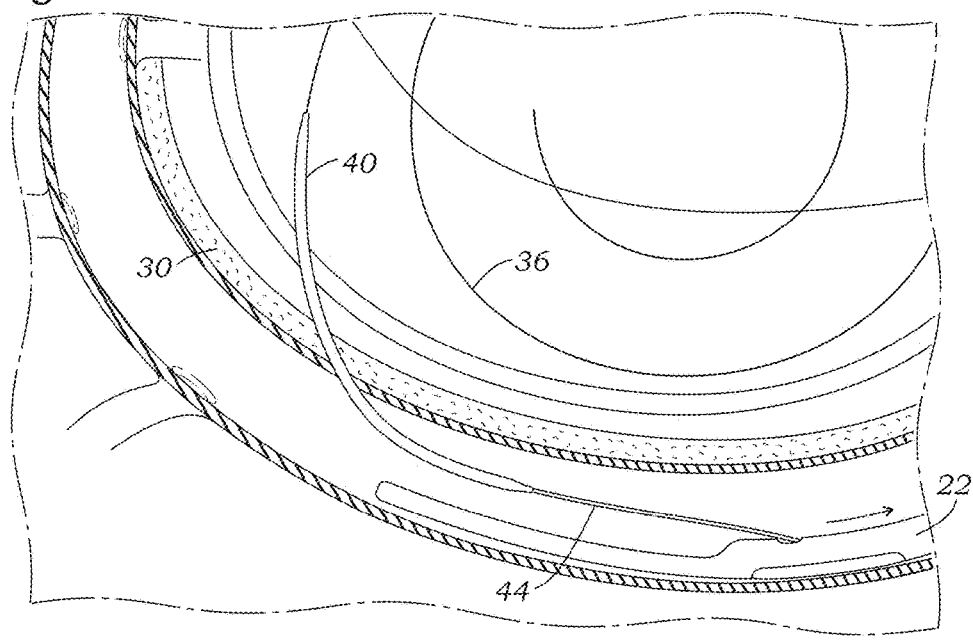
Figure 3J:
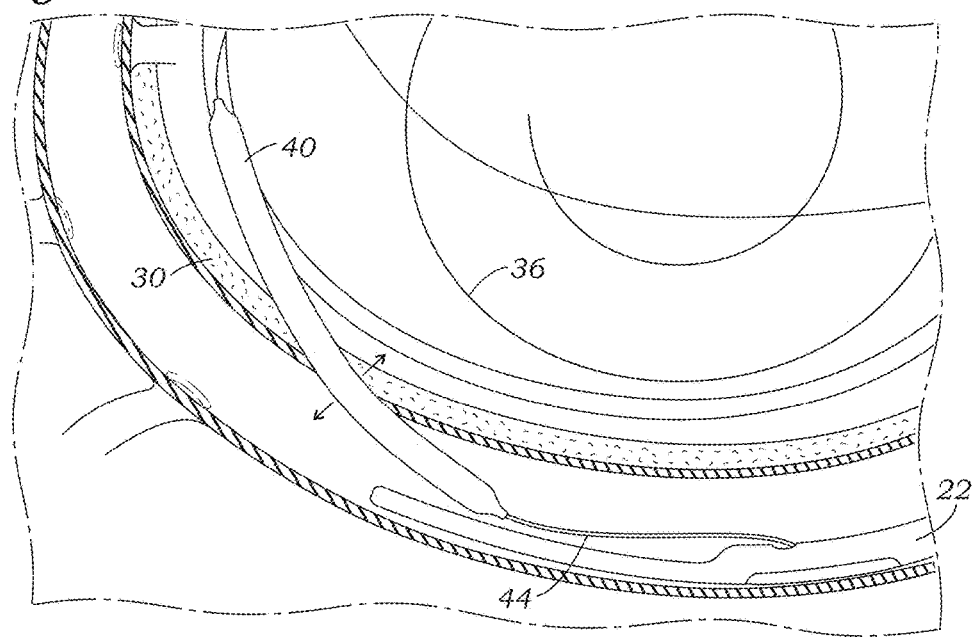
Figure 3K:
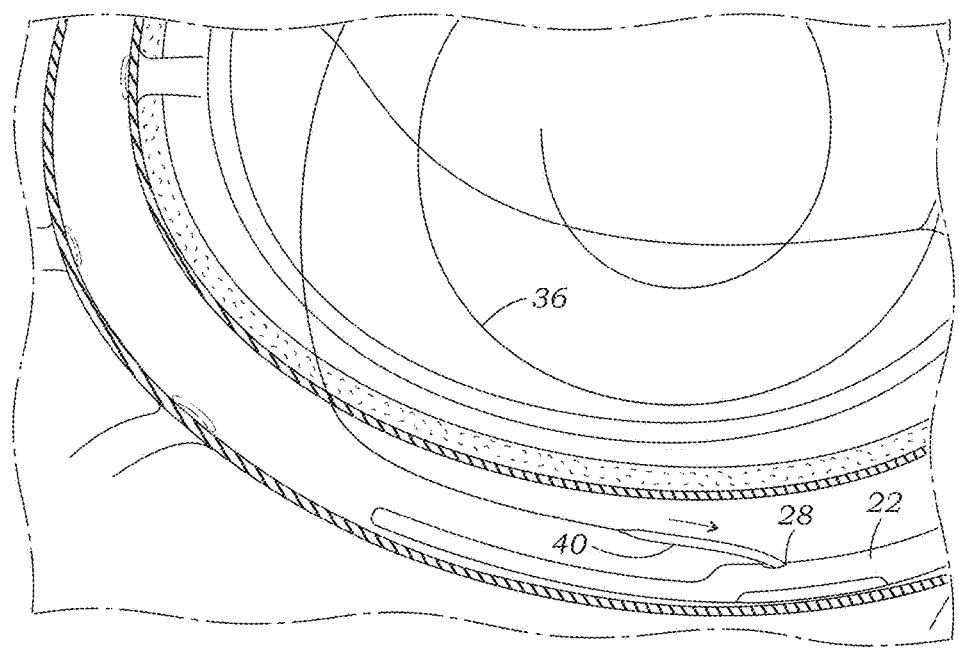
Figure 3L:
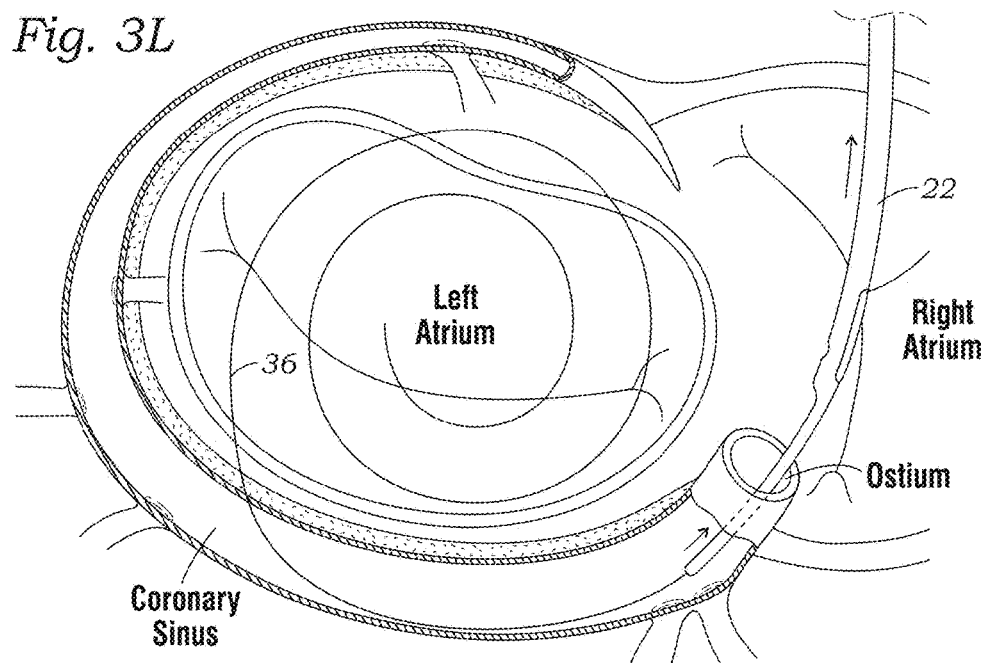
Figure 3M:
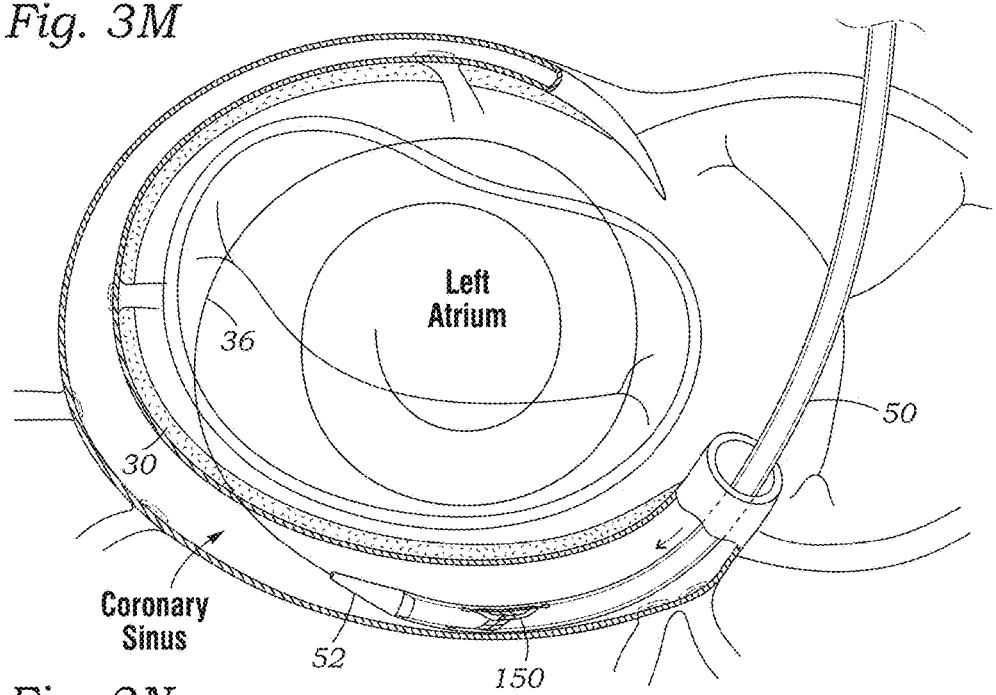
Figure 3N:
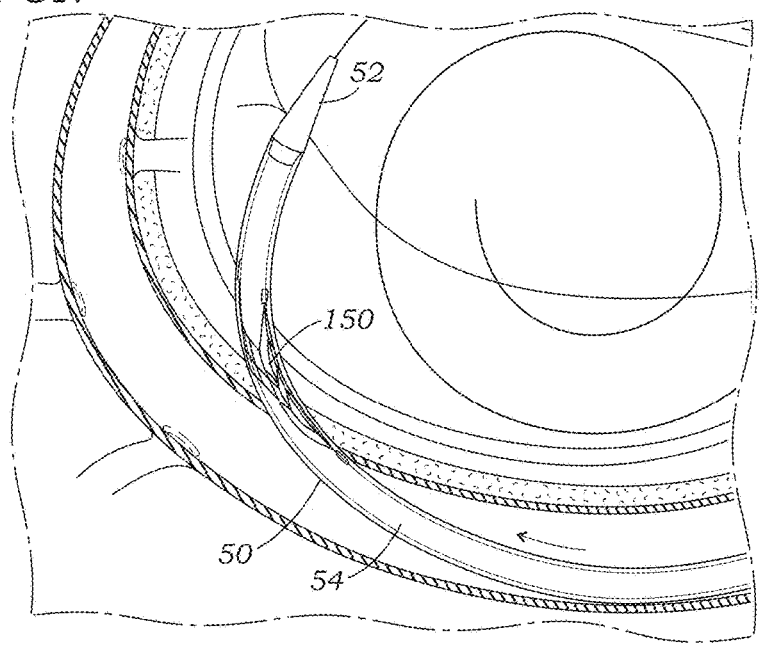
Figure 3O:
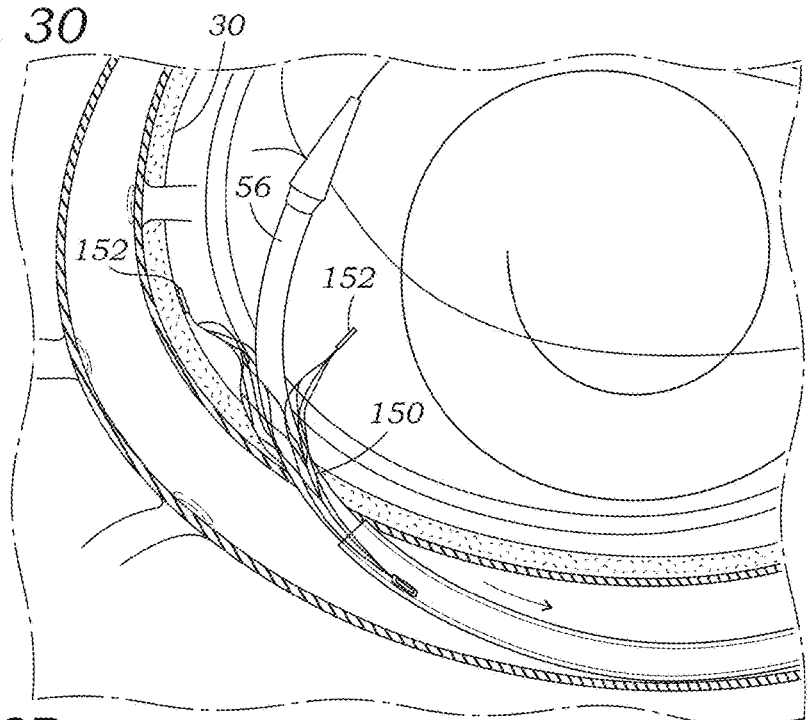
Figure 3P:
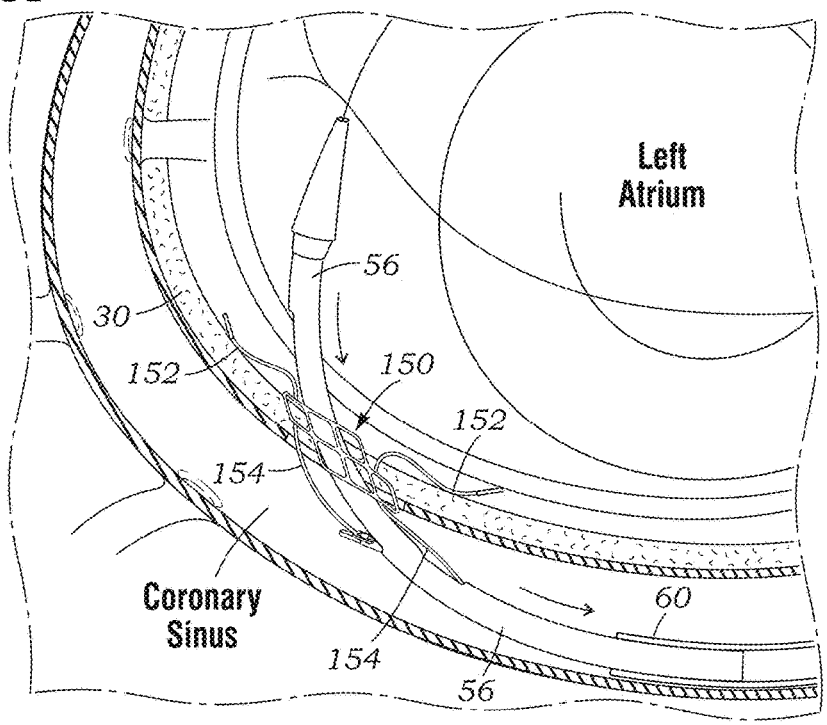
Figure 3Q:
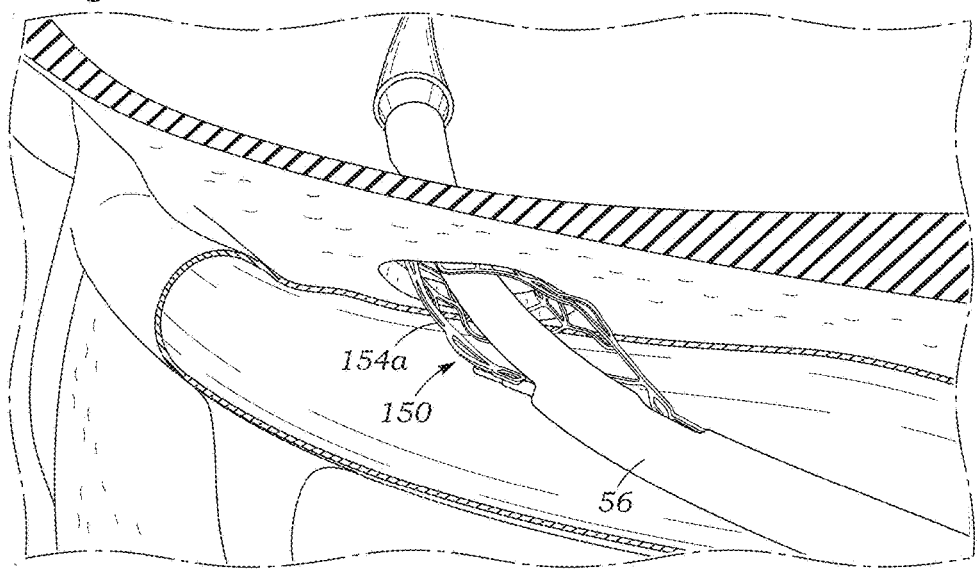
Figure 3R:
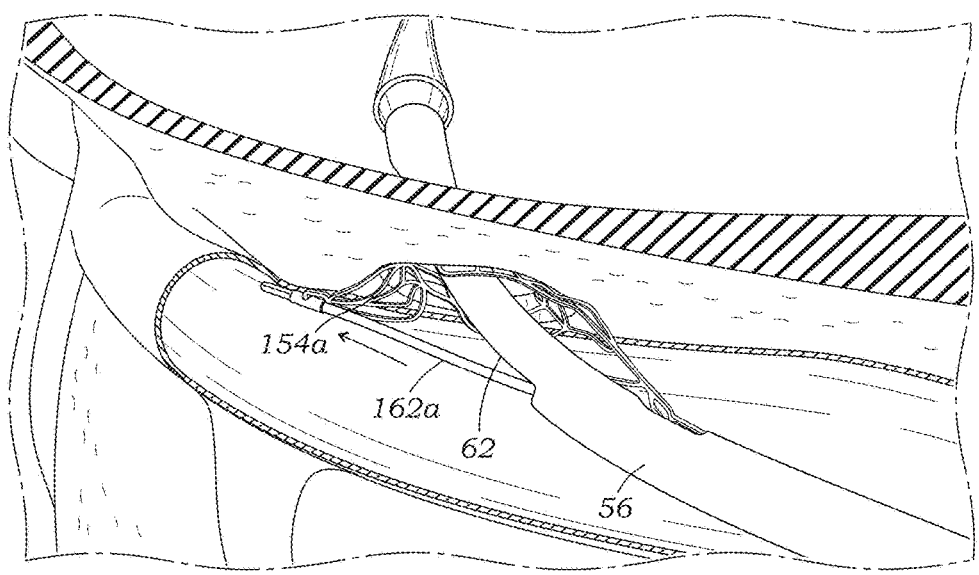
Figure 3S:
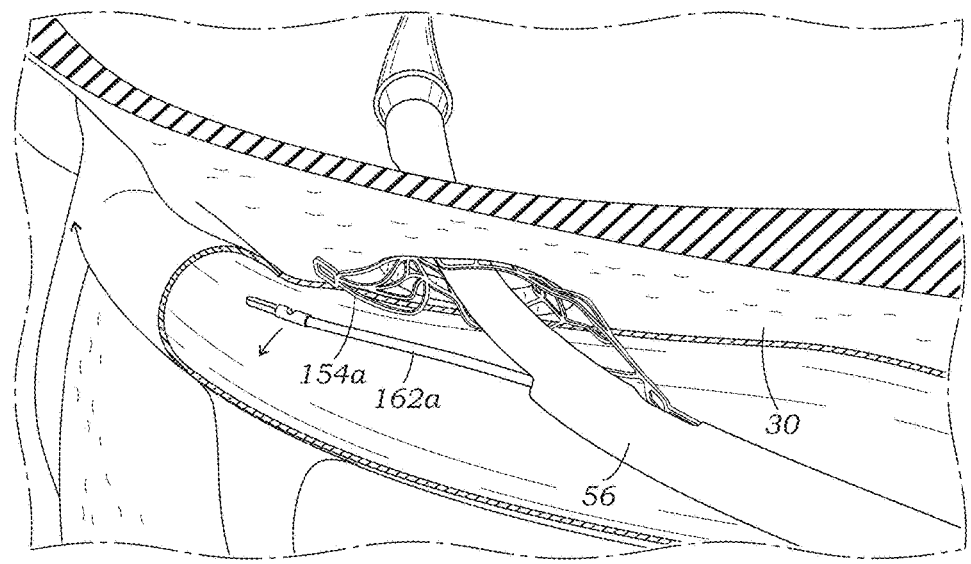
Figure 3T:
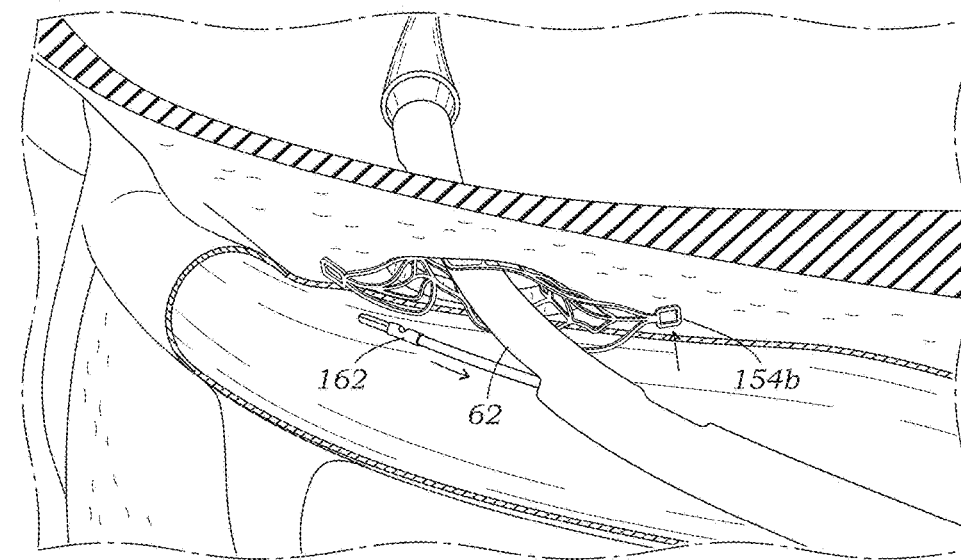
Figure 3U:
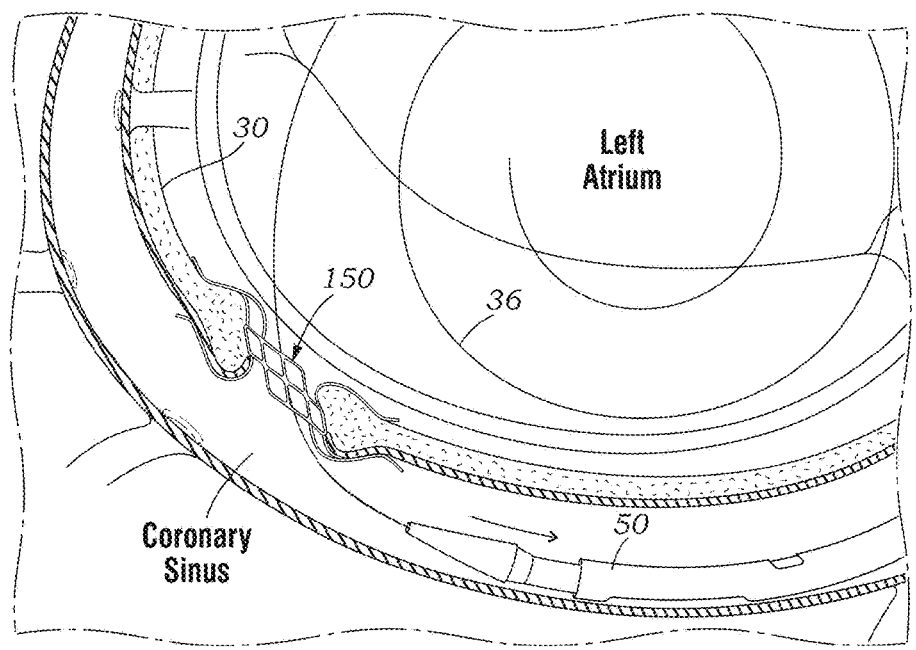
Figure 3V:
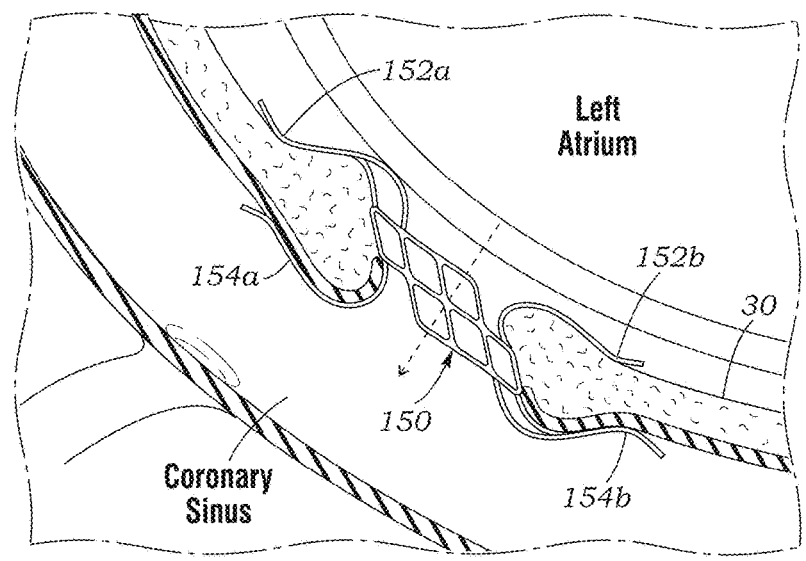

FIGS. 3A-3V are schematic views of steps in making a puncture hole through a wall of the coronary sinus and placement of a shunt between the coronary sinus and left atrium, as seen looking down on a section of the heart with the posterior aspect down.

Initially, FIG. 3A shows a guidewire 20 being advanced from the right atrium into the coronary sinus through its ostium or opening. A puncture catheter 22 is then advanced over the guidewire 20, as seen in FIG. 3B. Specifics of an exemplary puncture catheter 22 will be shown and described below with respect to FIGS. 12-13. The puncture catheter 22 is introduced into the body through a proximal end of an introducer sheath (not shown). As is customary, an introducer sheath provides access to the particular vascular pathway (e.g., jugular or subclavian vein) and may have a hemostatic valve therein. While holding the introducer sheath at a fixed location, the surgeon manipulates the puncture catheter 22 to the implant site.

At least a distal end of the puncture catheter 22 preferably has a slight curvature built therein, with a radially inner and a radially outer side, so as to conform to the curved coronary sinus. An expandable anchoring member 24 is exposed along a radially outer side of the catheter 22 adjacent an extreme distal segment 25 that may be thinner than or tapered narrower from the proximal extent of the catheter. Radiopaque markers 26 on the catheter 22 help the surgeon determine the precise advancement distance for desired placement of the anchoring member 24 within the coronary sinus. Desirably, the radiopaque markers 26 are C-shape bands that flank the proximal and distal ends of the anchoring member 24.

FIG. 3C shows radially outward deployment of the expandable anchoring member 24, which in the illustrated embodiment as a bulbous balloon but could also be a braided mesh. One advantage of a mesh is that it avoids excessive blockage of blood flow through the coronary sinus during the procedure, though the procedure typically does not take very long and a balloon is preferred. Other possible anchoring structures include Nitinol stent like structures, nitinol wire structure, etc. Expansion of the anchoring member 24 presses the radially inner curve of the catheter against the luminal wall of the coronary sinus. Again, the expandable anchoring member 24 is located adjacent the distal segment 25 of the puncture catheter 22, and expands opposite a needle port 28 formed in the radially inner side wall of the catheter. Consequently, the needle port 28 abuts the luminal wall and faces toward a tissue wall 30 between the coronary sinus and the left atrium. Preferably, guided by visualizing the radiopaque markers 26, the surgeon advances the catheter 22 so that the needle port 28 is located within about 2-4 cm into the coronary ostia. This places the subsequent puncture approximately above the "P2" portion of the posterior leaflet of the mitral valve (when looking at the inflow side of the valve the posterior leaflet has P1-P2-P3 cusps in a CCW direction, as seen in FIG. 3B). The anchoring member 24 may be centered diametrically across the catheter 22 from the needle port 28, or as shown may be slightly offset in a proximal direction from the needle port 28 to improve leverage.

The curvature at the distal end of the puncture catheter 22 aligns to and "hugs" the anatomy within the coronary sinus and orients the needle port 28 inward, while the anchoring member 24 holds the catheter 22 in place relative to the coronary sinus. Subsequently, as seen in FIG. 3D, a puncture sheath 32 having a puncture needle 34 with a sharp tip advances along the catheter 22 such that it exits the needle port 28 at an angle from the longitudinal direction of the catheter and punctures through the wall 30 into the left atrium. The anchoring member 24 provides rigidity to the system and holds the needle port 28 against the wall 30. Preferably, the puncture needle 34 has a flattened configuration to form a linear incision, and is mounted on the distal end of an elongated wire or flexible rod (not shown) that passes through a lumen of the puncture sheath 32.

FIG. 3E illustrates proximal retraction of the puncture needle 34 from within the puncture sheath 32. The puncture needle 34 is removed completely from the catheter 22, which leaves open a lumen within the puncture sheath 32.

FIG. 3F then shows advancement of a second guidewire 36 through the puncture sheath 32 lumen and into the left atrium. FIG. 3G illustrates removal of the puncture sheath 32 from the left atrium and into the puncture catheter 22, which leaves just the guidewire 36 extending through the coronary sinus and into the left atrium. During these steps, the anchoring member 24 remains expanded against the opposite luminal wall of the coronary sinus for stability.

FIG. 3H shows a puncture expander 40 advanced along the guidewire 36 and through the tissue wall 30 into the left atrium. The puncture expander 40 may be an elongated inflatable balloon having a tapered distal end 42.

FIG. 3I then shows retraction of the puncture catheter 22 from around the elongated puncture expander 40. The puncture expander 40 and a proximal inflation tube 44 ride over the guide wire 36 and are held in place during retraction of the catheter 22. The puncture catheter 22 retracts just far enough to avoid interference with the expander 40. FIG. 3J illustrates radially outward inflation of the puncture expander 40 so as to widen the puncture through the tissue wall 30.

FIG. 3K then shows retraction of the puncture expander 40 through the needle port 28 and into the puncture catheter 22. Subsequently, the entire puncture catheter 22 is removed along the guide wire 36 from the body, as seen in FIG. 3L. Although puncturing a hole between the coronary sinus and the left atrium as well as delivering the shunt may be accomplished with a single access device, the present method contemplates two different devices performing the separate tasks.

FIG. 3M thus shows introduction of a shunt deployment or delivery catheter 50 having a soft, tapered distal tip 52 advancing along the guide wire 36 that remains bridging the tissue wall 30 between the coronary sinus and the left atrium. FIG. 3N then shows the delivery catheter 50 advanced through the puncture in the tissue wall 30 into the left atrium, which passage is facilitated by widening of the puncture as described above and the soft, tapered distal tip 52. The delivery catheter 50 is shown in section in these views to illustrate a desired position of an expandable shunt 150 therein, just proximal to the distal tip 52. The expandable shunt 150 is shown in a collapsed, generally tubular configuration, described in more detail below, which facilitates passage through the lumen 54 of the catheter 50. Actuating rods extending through the lumen 54 and connected to the expandable shunt 50 are not shown in some of these illustrations for clarity, but are also described below.

FIG. 3O depicts an initial deployment of the shunt 150 wherein a pair of distal flanges 152 expands within the left atrium into contact with the tissue wall 30. This expansion is initiated by retraction of an outer sheath 60 of the delivery catheter 50 relative to an inner sheath 56. As will be described below with respect to FIG. 14B, the shunt 150 is located in the annular space between the inner sheath 56 and outer sheath 60. The inner sheath 56 passes through a central flow passage of the shunt 150. The shunt 150 collapses into a generally tubular configuration between the two sheaths and its flanges spring open as seen in FIGS. 3O and 3P when the restraining outer sheath 60 retracts. As will be described below, the flanges 152 expand generally in opposite directions in a common plane to form a T-shape, as opposed to expanding in a circular fashion which would form an annular flange. Radiopaque markers on the flanges 152 may be provided to facilitate positioning immediately within the left atrium.

FIG. 3P illustrates further deployment of the expandable shunt 150 just before a pair of proximal flanges 154 expands within the coronary sinus into contact with the wall 30. More particularly, the physician retracts the entire inner sheath 56 and shunt 150 until the two distal flanges 152 come into contact with the tissue wall 30. This can be felt by tactile feedback, or by once again confirming the position of the distal flanges 152 by radiopaque visualization. The outer sheath 60 is also shown retracted farther proximally to expose a pair of proximal flanges 154. At this stage in deployment of the shunt 150, the proximal flanges 154 are retained by actuating rods and prevented from expanding within the coronary sinus.

FIG. 3Q is an enlarged view from the perspective of the coronary sinus to better illustrate deployment of the proximal flanges 154. As described above, the inner sheath 56 is retracted so that the distal flanges 152 are in intimate engagement with the tissue wall 30 on the left atrial side. The proximal flanges 154 remain constrained generally aligned with the inner sheath 56.

FIG. 3R shows distal advancement of a first control or actuating rod 162a from within the inner sheath 56. The first actuating rod 162a emerges from a side opening 62 in the inner sheath 56, and is coupled to a leading or first proximal flange 154a such that the flange is permitted to expand into its relaxed position as shown. Once the flange 150 is believed to be positioned within the puncture wound, but prior to its release from the delivery catheter 50, a contrast injection is desirably made in the vicinity to see whether the shunt is properly positioned. That is, contrast media visible in the gaps between the opposed flanges 152, 154 indicates that the flanges are not on opposite sides of the tissue wall 30. The shunt 150 can thus be further manipulated to changing position.

FIG. 3S then shows release of the first proximal flange 154a by the first actuating rod 162a, thus permitting the flange to resiliently contact the tissue wall 30 (or at least the luminal surface of the coronary sinus). The physician then causes retraction of the first actuating rod 162a into the side opening 62, as seen in FIG. 3T. Subsequently, a second control or actuating rod (not shown) releases the trailing or second proximal flange 154b, which also permits it to resiliently contact the tissue wall 30. At this point, the shunt 150 is entirely free from the delivery catheter 50, though the inner sheath 56 remains extending through the central flow passage of the shunt. The opposed leading flanges 152a, 154a form a clamping pair of flanges, as do the opposed trailing flanges 152b, 154b. As will be explained, the clamping pairs of flanges apply a small compressive force to the tissue wall 30 hold the shunt 150 in place, though the gaps separating the clamping pairs of flanges is desirably calibrated to avoid excessive clamping or necrosis of the tissue.

The delivery catheter 50 is shown being retracted along the guidewire 36 in FIG. 3U, such that the shunt 150 is fully deployed between the left atrium and the coronary sinus. The guidewire 36 is then retracted as well. FIG. 3V illustrates full deployment with the proximal pair of flanges 154 expanded within the coronary sinus into clamping contact with the wall 30. The primary retention mechanism for the shunt 150 comes from the geometrical constraint of the design—the length of the flanges 152, 154 prevent it from being pulled through the hole. Secondary to that is a radial force exerted outward on the puncture from the central flow tube 166 of the implant (described below). The opposed clamping forces of the flanges 152, 154 also help hold the shunt 150 in place, but are not essential. Elevated Left Atrial Pressure (LAP) can thus be ported through the implanted shunt 150 into the coronary sinus as indicated by the dashed arrow in FIG. 3V. By creating an opening between the left atrium and the coronary sinus, blood will flow from the higher pressure left atrium (usually >8 mmHg) to the lower pressure coronary sinus (usually <8 mmHg).

Previous methods (e.g., available from V-Wave Ltd. of Hod-Hasharon, Israel & Corvia Medical of Tewksbury, Mass. (previously DC Devices, Inc.)) to reduce LAP have instead utilized a shunt between the left atrium and the right atrium, through the interatrial septum therebetween. This is a convenient approach, as the two structures are adjacent and transseptal access is common practice. However, there is always a possibility of emboli travelling from the right side of the heart to the left, which presents a stroke risk. This event should only happen if the right atrium pressures go above left atrium pressures; primarily during discrete events like coughing, sneezing, Valsalva maneuver, or bowel movements. The anatomical position of the septum would naturally allow emboli to travel freely between the atria if a shunt was present and the pressure gradient flipped. This can be mitigated by a valve or filter element in the shunt, but there is still a risk that emboli will cross over.

Shunting to the coronary sinus offers some distinct advantages, primarily that the coronary sinus is much less likely to have emboli present for several reasons. First, the blood draining from the coronary vasculature into the right atrium has just passed through capillaries, so it is essentially filtered blood. Second, the ostium of the coronary sinus in the right atrium is often partially covered by a pseudo-valve called the Thebesian Valve. The Thebesian Valve is not always present, but some studies show it is present in >60% of hearts and it would act as a natural "guard dog" to the coronary sinus to prevent emboli from entering in the event of a spike in right atrium pressure. Third, pressure gradient between the coronary sinus and the right atrium into which it drains is very low, meaning that emboli in the right atrium is likely to remain there. Fourth, in the event that emboli do enter the coronary sinus, there will be a much greater gradient between the right atrium and the coronary vasculature than between the right atrium and the left atrium. Most likely emboli would travel further down the coronary vasculature until right atrium pressure returned to normal and then the emboli would return directly to the right atrium.

Some additional advantages to locating the shunt between the left atrium and the coronary sinus is that this anatomy is less mobile than the septum (it is more stable), it thus preserves the septum for later transseptal access for alternate therapies, and it could potentially have other therapeutic benefits. By diverting left atrial blood into the coronary sinus, sinus pressures may increase by a small amount. This would cause blood in the coronary vasculature to travel more slowly through the heart, increasing perfusion and oxygen transfer, which would be more efficient and also could help a dying heart muscle to recover. There is a device designed to do this very thing, the Neovasc Reducer. The preservation of transseptal access also is a very significant advantage because HF patients often have a number of other comorbidities like Atrial Fibrillation (AF) and Mitral Regurgitation (MR) and several of the therapies for treating these conditions require a transseptal approach.

The shunt 150 may also be positioned between other cardiac chambers, such as between the pulmonary artery and right atrium. The shunt 150 is desirably implanted within the wall of the pulmonary artery using the deployment tools described herein, with the catheters approaching from above and passing through the pulmonary artery. As explained above, pulmonary hypertension (PH) is defined as a rise in mean pressure in the main pulmonary artery. Blood flows through the shunt 150 from the pulmonary artery into the right atrium if the pressure differential causes flow in that direction, which attenuates pressure and reduces damage to the pulmonary artery. The purpose is to attenuate pressure spikes in the pulmonary artery. The shunt 150 may also extend from the pulmonary artery to other heart chambers (e.g., left atrium) and/or blood vessels. Although not preferred or shown, the shunt 150 may further contain a one-way valve for preventing backflow, or a check valve for allowing blood to pass only above a designated pressure.

The present application discloses a new expandable shunt, a tool for preparing the wall between the left atrium and the coronary sinus for implant of the shunt, and a tool for delivering the shunt. Each of these devices will be described below.

FIGS. 4A-4H illustrates a sequence of deployment of an exemplary expandable shunt 150 through a delivery tube or catheter 142. The shunt 150 is expelled from the distal tip 144 of the catheter 142 and naturally self-expands due to its inherent springiness or flexibility. In a preferred embodiment, the shunt 150 is formed from a super elastic material such as Nitinol. The delivery catheter 142 in this sequence is shown as a tubular member from the distal end of which the shunt 150 is expelled, unlike the catheter shown in the sequence of FIGS. 3N-3T, above, or in FIGS. 14A-14B below. It should be understood, therefore, that the expandable shunt 150 can be implanted and the various methods described herein can be performed using a number of different delivery catheters.

Figure 4A:
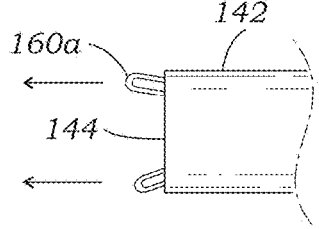
FIGS. 4A-4H illustrates a sequence of deployment of an exemplary expandable shunt through a sheath using a pair of actuating rods.
Figure 4B:
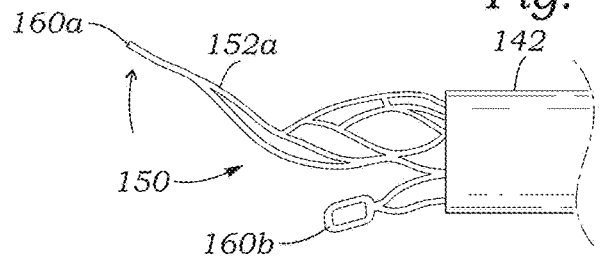
Figure 4C:
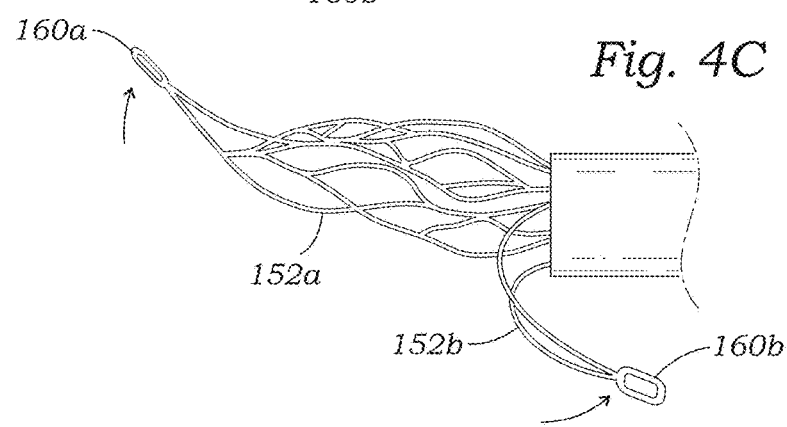
Figure 4D:
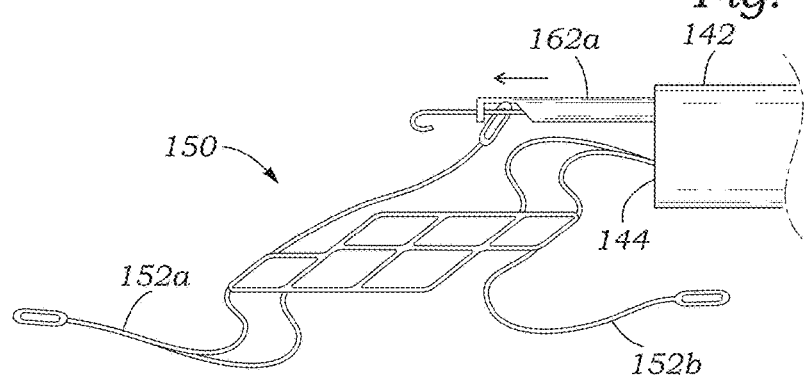

FIGS. 4A-4D show the shunt 150 gradually advancing from the distal tip 144 and expanding in stages. The reader will reference FIGS. 6A-6E for a clearer understanding of the various components of the expandable shunt 150. In FIG. 4A, a terminal end 160a of a leading or first distal flange 152a is seen emerging distally from the catheter 142 followed by the rest of the flange in FIG. 4B. FIG. 4B shows a terminal end 160b of a trailing or second distal flange 152b emerging from the catheter 142. FIG. 4C shows the second distal flange 152b curling in a proximal direction due to its inherent shape memory, while the first distal flange 152a continues to extend in a distal direction. Eventually, both the first and second distal flanges 152a, 152b are fully expelled from the catheter 142 and extend generally in opposite directions, as shown in FIG. 4D. The first distal flange 152a is longer than the second distal flange 152b.

It should be noted that the location of the distal tip 144 of the catheter 142 enables deployment of the first and second distal flanges 152a, 152b within the left atrium. In this way, the flanges 152a, 152b may be expanded into contact with the wall 30 on the left atrial side. Subsequently, the catheter 142 is retracted until the distal tip 144 is located in the coronary sinus, and then the proximal flanges 154 may be deployed, as will be explained. (The reader will notice that the shunt 150 in these views is inverted from the delivery sequence of FIGS. 3N-3V, such that the distal flanges 152a, 152b are down while the proximal flanges 154a, 154b are up.) The offset lengths of the opposed flanges 152, 154 reduces excessive pinching of the tissue wall 30 therebetween.

FIG. 4D also shows a first control or actuating rod 162a projecting from the distal tip 144 of the catheter 142. The first actuating rod 162a and a second control or actuating rod 162b, seen first in FIG. 4E, engage different locations on the expandable shunt 150 and control its expulsion from the catheter 142. The first actuating rod 162a engages a terminal end 164a of a leading or first proximal flange 154a, while the second actuating rod 162b engages a terminal end 164b of a trailing or second proximal flange 154b. The first proximal flange 154a is shorter than the second proximal flange 154b. The first and second actuating rods 162a, 162b are configured to slide axially within the catheter 142 independently of one another. Various mechanisms are known for displacing such rods along catheters and thus will not be described in detail herein.

Figure 4E:
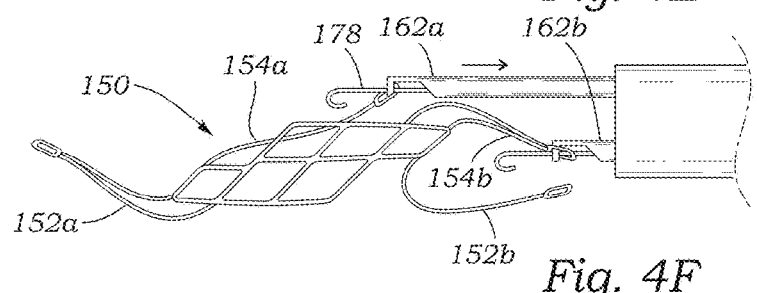
Figure 4F:
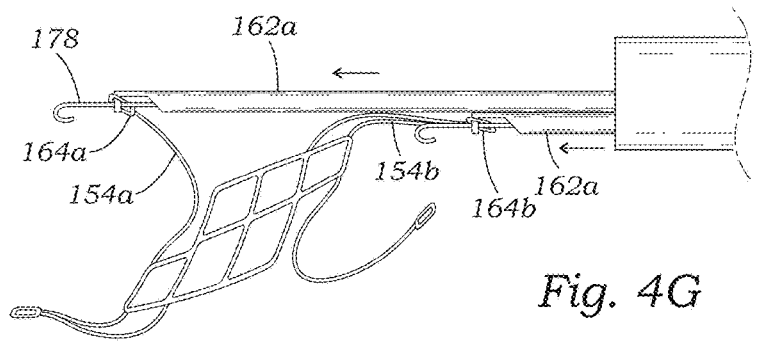
Figure 4G:
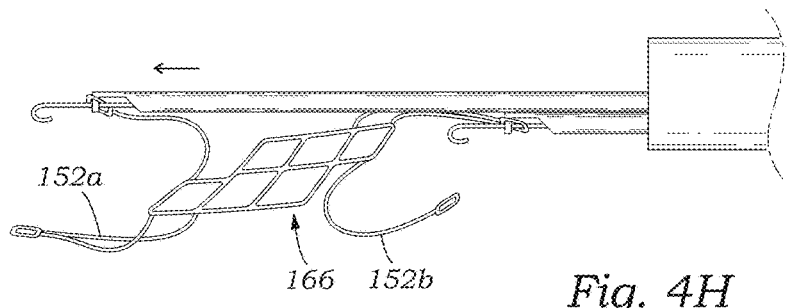

As seen in FIGS. 4F and 4G, the first actuating rod 162a continues to advance the terminal end 164a of the first proximal flange 154a, but the second actuating rod 162b halts so as to stop advancement of the terminal end 164b (see FIG. 4H) of the second proximal flange 154b. This permits the two flanges 154a, 154b to separate so as to allow the shunt 150 to assume its relaxed, expanded configuration. More particularly, a central flow tube 166 (or "barrel" portion) gradually opens until the fully expanded state is reached. The two actuating rods 162a, 162b may carry thin elongated release rods 178 which may be retracted to release the rods from engagement with the proximal flanges 154a, 154b.

Figure 4H:
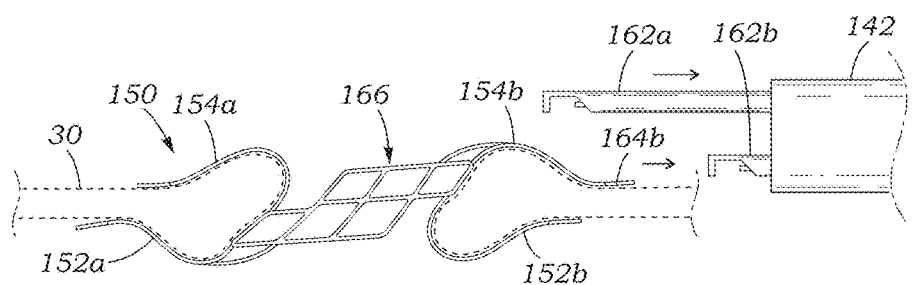

FIG. 4H shows the shunt 150 in its fully expanded state just after detachment of the two actuating rods 162a, 162b. The distal and proximal flanges 152, 154 secure the shunt 150 on opposite sides of the wall 30 between the coronary sinus and the left atrium (see FIGS. 3U and 3V), with a flow axis of the central flow tube 166 aligned generally perpendicular to the wall so as to maintain an open flow path between the coronary sinus and the left atrium.

Figure 5A:
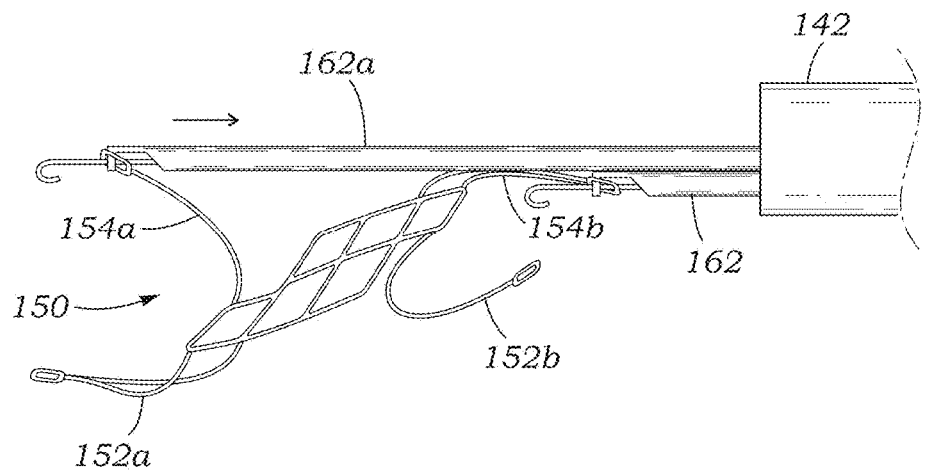
FIGS. 5A-5C are several views of the expandable shunt being retracted into the delivery catheter.
Figure 5B:
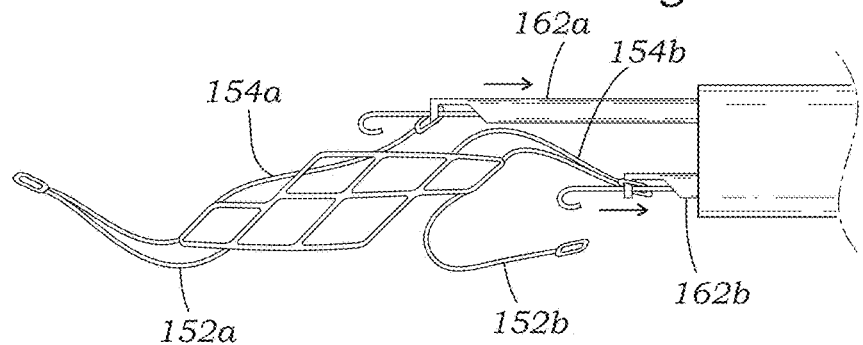
Figure 5C:
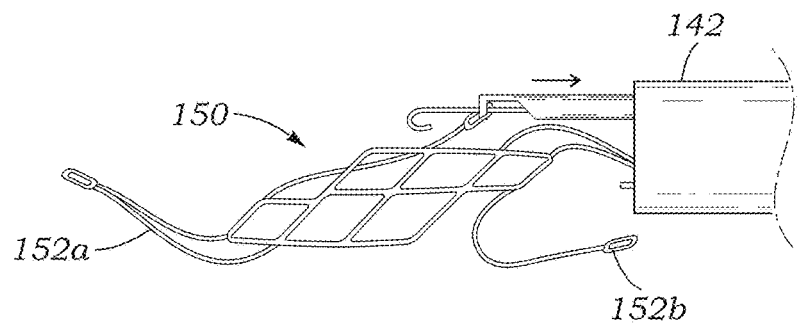

FIGS. 5A-5C are several views of the expandable shunt 150 being retracted into the delivery catheter 142. In case the placement of the shunt 150 fails or is unsatisfactory, and before the first and second actuating rods 162a, 162b detach therefrom, the shunt can be retrieved. In particular, proximal movement of the first actuating rod 162a as seen in FIG. 5A pulls the first proximal flange 154a so as to start collapse of the shunt. Further retraction of the first actuating rod 162a and then of the second actuating rod 162b as seen in FIGS. 5B and 5C continues the collapse, essentially in the reverse of the deployment steps of FIGS. 4A-4G. Placement of the shunt 150 may then be retried, or a different shunt used altogether by replacement of the entire deployment system.

Figure 6A:
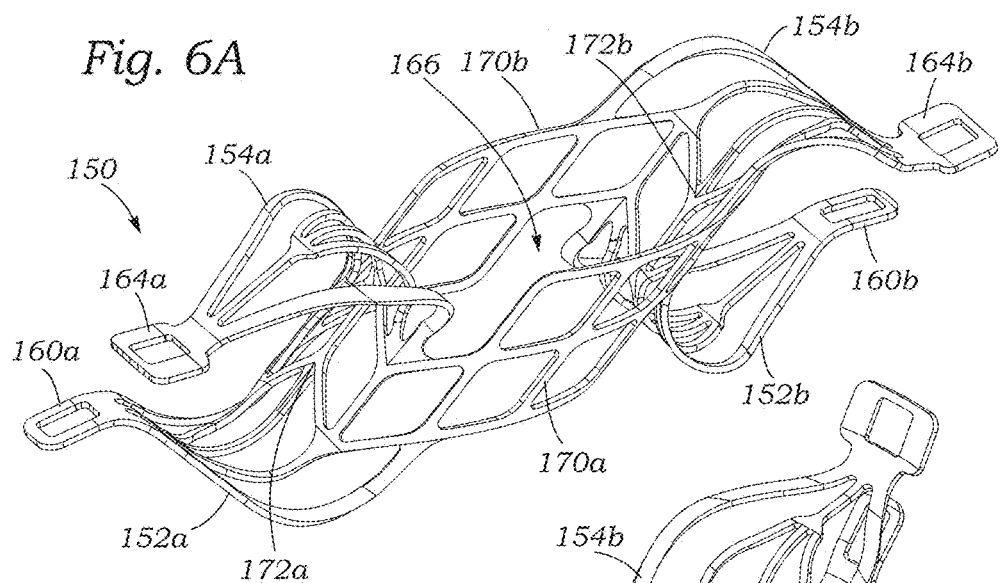
Figure 6B:
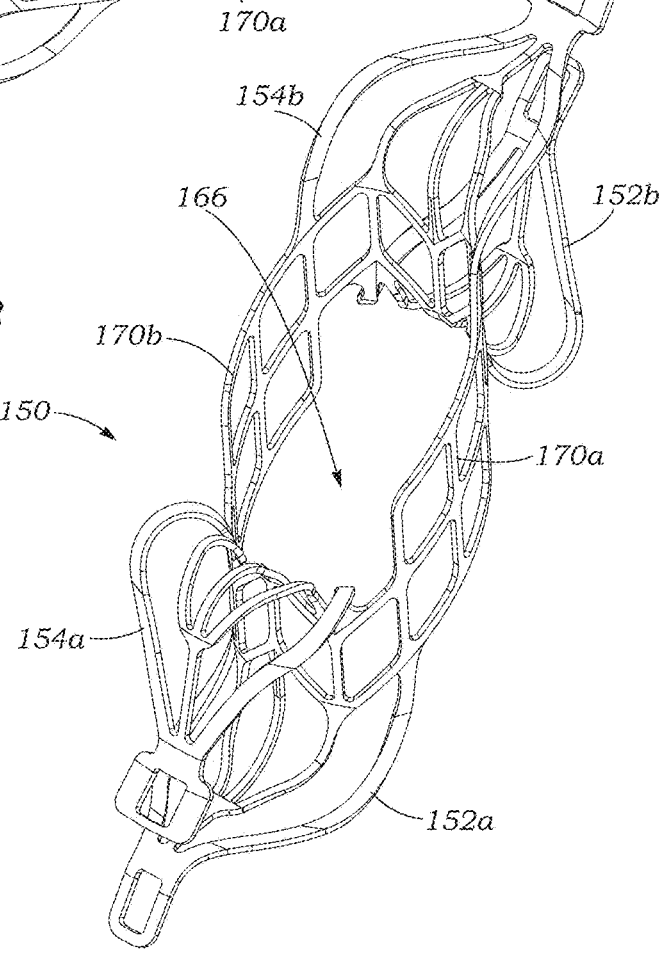

FIGS. 6A-6D show greater details of the exemplary expandable shunt 150 in an expanded configuration, while FIG. 6E is a view looking through the central flow tube 166 along an angle of tilt. When expanded, the central flow tube 166 of the shunt 150 defines a generally circular or oval opening, as seen from above in FIG. 6D, which holds the sides of the puncture open and forms the blood flow path between the coronary sinus and the left atrium. The central flow tube 166 is partly formed by a pair of side walls 170a, 170b defined by a generally parallelogram arrangement of thin struts 179 that forms an array of parallelogram-shaped cells or openings 180. Indeed, the entire shunt 150 is formed by super-elastic struts that are capable of compression into the catheter 142 and subsequent expansion back to the relaxed shape as shown.

Formation of the shunt 150 using a plurality of interconnected struts forming cells therebetween is primarily to increase the flexibility of the shunt which enables it compression and then expansion at the implant site. The interconnected struts around the central flow tube 166 provide a cage of sort which is sufficient to hold the tissue at the puncture open. Desirably, the interconnection of the struts omits any sharp corners or points which might snag tissue when the shunt is being manipulated through the puncture.

End walls 172a, 172b of the central flow tube 166 connect the side walls 170a, 170b and extend between the distal and proximal flanges 152, 154 on each side. The side walls 170a, 170b and end walls 172a, 172b together define a tubular lattice which as will be seen is angled or tilted. The end walls 172a, 172b also comprise thin struts 179 extending at a slight angle from a perpendicular axis 174 through the central flow tube 166. That is, as seen in FIG. 6C, an imaginary reference axis 174 may be drawn generally perpendicular to a horizontal reference plane HP, such that an angled axis 176 is defined by the angled end walls 172a, 172b of the central flow tube 166. Indeed, the central flow tube 166 extends at an angle α from the perpendicular axis 174. The angle α may be between 30-60°, and more particularly is about 45°. The horizontal reference plane HP is generally defined by the wall 30 between the coronary sinus and the left atrium (FIG. 3U); though of course the wall is not simply planar. Although oriented at this slight angle α, the opening as seen in FIG. 6D formed by the central flow tube 166 is generally perpendicular to the wall 30 and permits direct blood flow between the coronary sinus and the left atrium. That is, the angled flow tube 166 is wide and short enough such that proper shunting occurs, as if the flow tube were perpendicular to the tissue wall 30.

FIG. 6E is a view looking along angled axis 176 of the central flow tube 166 of the expanded shunt 150. The axis 176 defines the "tilt" of the expanded shunt 150, in that it defines the angle that the central flow tube 166 makes with the horizontal reference plane HP, which again lies generally in the plane of the tissue wall through which the shunt passes. It can thus be seen from FIG. 6E that the struts of the central flow tube 166 define a tubular or circular lattice, even if the struts that form the tube do not form a contiguous wall surface (there are open cells). The tilt of the expandable shunt 150 facilitates collapse into the delivery catheter 142, and then expansion of the flanges 152, 154 on both sides of the tissue wall 30. It should be noted that the central flow tube 166 remains essentially unchanged between the collapsed and expanded states of the shunt 150, whereas the flanges 152, 154 transition in and out of alignment with the angled flow tube.

FIG. 6F is a view similar to FIG. 6E through an alternative shunt having an oval-shaped flow tube 166'. The characteristics of the shunt are the same as with the shunt 150, though the side walls are elongated in comparison to form the oval channel. This alternative may be useful for larger punctures while the shunt still collapses down to a relatively small delivery profile. An oval-shaped delivery catheter may be used to deploy the shunt or a standard tubular catheter is used with the shunt conforming therein.

Referring back to FIG. 6C, each of the distal and proximal flanges 152, 154 curls outward from the end walls 172a, 172b and ends up pointing approximately radially away from the imaginary reference axis 174 through the central flow tube 166. More specifically, the two distal flanges 152a, 152b extend away from each other as do the two proximal flanges 154a, 154b. As seen best in FIG. 6D, the flanges 152, 154 extend outward from the central flow tube 166 in opposite directions parallel to a central vertical plane VP, such that the shunt 150 is generally elongated longitudinally but is relatively narrow laterally. Stated another way, the distal and proximal flanges 152, 154 are not annular/circular but instead extend outward generally in only one plane. FIG. 6C shows that each pair of flanges 152, 154 forms somewhat of a T-shape on that end of the central flow tube 166, and the entire side view resembles a sideways H-shape. This is in contrast to a spool shape which would be the case if the flanges were annular. This elongated or linear shape for the expandable shunt 150 means that when compressed it elongates along a line so as to better fit within the catheter 142.

Of course, the struts of the super-elastic flanges 152, 154 are curved, not solid and not geometrically precise, but what they are clearly not is annular/circular. Likewise, the central flow tube 166 is tilted as opposed to extending straight between the flanges 152, 154, but the H-shaped analogy remains.

As indicated in FIG. 6D, the shunt 150 has a maximum lateral width W approximately equal to the diameter of the central flow tube 166, while the lateral width w of the flanges 152, 154 is slightly less. In one embodiment, the maximum lateral width W of the shunt 150 is about 7.5 mm, while the lateral width w of the flanges 152, 154 is about 7.0 mm.

As seen best from above in FIG. 6D, each flange 152, 154 has a somewhat triangular plan view shape with a wide base at the central flow tube 166 narrowing to an apex at the terminal ends 160, 164. The elongated shape of the shunt 150 permits it to collapse down to a more linear profile so as to fit within a relatively small catheter 142. The reader will notice that the distal and proximal flanges 152, 154 are entirely curved in configuration which also facilitates their collapse and expansion. That is, the struts that form the flanges 152, 154 are designed so that they easily collapse into a compact size that fits into the catheter 142 when acted on by the first and second actuating rods 162a, 162b. Finally, the shunt 150 is inversely symmetrical across the horizontal plane HP in FIG. 6C, which is also a midplane of the shunt. That is, the first distal flange 152a is generally the same size and shape as the second proximal flange 154b, and the first proximal flange 154a is generally the same size and shape as the second distal flange 152b, and so on.

Additionally, each pair of distal and proximal flanges 152, 154 on each side of the central flow tube 166 converges toward each other so that their terminal ends 160, 164 are closer together than the ends connected to the end walls 172a, 172b. This enables the end walls 172a, 172b to have a length that approximates thickness of the wall 30 between the coronary sinus and the left atrium (see FIG. 3V). The terminal ends 160, 164 of the flanges 152, 154 are spaced closer together so that they flex outward and grip the wall, thus helping to maintain the shunt 150 in place. FIG. 3V shows the terminal ends 160, 164 squeezing the tissue wall 30. Of course, the super-elasticity of the flanges 152, 154 means they are highly flexible and so they will not apply excessive clamping forces to the wall 30 which might cause necrosis. Furthermore, the offset lengths of the opposed flanges 152, 154 reduces direct pinching of the tissue wall 30 therebetween.

The terminal ends 164 of the proximal flanges 154 are shaped for rapid engagement with the first and second actuating rods 162a, 162b. In particular, the terminal ends 164a, 164b each define an eyehole or other closed shape so as to be easily gripped by the first and second actuating rods 162a, 162b. In the illustrated embodiment, each of the terminal ends 164a, 164b defines a generally rectangular closed hole through which a slim rod may be passed. Although not shown in great detail, FIGS. 4E and 4F show the slim release rods 178 passed through the ends 164. An engagement portion of each of the first and second actuating rods 162a, 162b provides a hook, notch or recess shaped to closely receive and hold the terminal ends 164a, 164b when the slim rods 178 are thus engaged. To release the terminal ends 164a, 164b, the slim rods 178 are retracted relative to the remainder of the actuating rods 162, as seen in FIG. 4H. Of course, numerous other configurations of this gripping arrangement may be utilized, the illustrated embodiment being exemplary only.

FIGS. 7A and 7B are elevational views of the exemplary expandable shunt illustrating certain preferred dimensions and advantageous structural features. An overall length L of the shunt 150 may vary, and in one embodiment is between about 25-30 mm, preferably 28±1 mm. The perpendicular reference axis 174 extends through a central point in the side walls 170 and can be used to quantify the lengths of each of the flanges 152, 154. There is a shorter pair and a longer pair of flanges, one on each side of the horizontal midplane HP. A first length $L_1$ of the shorter pair of flanges is between about 9-13 mm, preferably 11±0.7 mm. This length is believed to be short enough to enable the shorter proximal flange 154 to rotate almost 180° within the coronary sinus. A second length L2 of the longer pair of flanges is between about 12-16 mm, preferably 14±0.5 mm. The length of the longer distal flange 152 is preferably limited to avoid touching the mitral valve leaflet. It should be noted that the terminal ends of the shorter flanges end up approximately parallel to the horizontal midplane HP, while the terminal ends of the longer flanges may also be parallel but are preferably are angled slightly away from the horizontal midplane HP by an angle θ of between 0-20°.

FIG. 7A also shows various vertical dimensions of the expanded shunt 150, including an overall height H of between about 5-10 mm, more preferably about 6.7±1.0 mm. A first height dimension $H_1$ of the longer pair of flanges from the midplane HP is between 3-5 mm, more preferably about 3.4 mm, while a second height dimension $H_2$ of the shorter pair of flanges is between 2-4 mm, more preferably about 2.4±0.5 mm. A gap G formed between the terminal ends of each pair of opposed flanges is between about 0-5 mm, and more particularly about 1.25±1.5 mm. It should be noted that even with a gap G of 0 mm, the two opposed flanges are independently deployed on opposite sides of the tissue wall, which may be relatively thin. It is expected that the tissue wall 30 has a thickness of between about 2-4 mm, and the gap G will be dimensioned accordingly. Finally, a height dimension h of the central flow tube 166 (as defined by the height of the side walls 170) is between 3-5 mm, and more particularly about 3.9±0.2 mm.

FIG. 7B is another elevational view of the expanded shunt 150 which illustrates a preferred configuration of the thin struts 179 making up the central flow tube 166. As mentioned above, the flow tube 166 is defined by a generally parallelogram arrangement of struts that forms an array of parallelogram-shaped cells or openings 180. The side walls 170 are generally circumscribed by a large parallelogram 182 that is tilted in the same direction as the tilted axis 176 through the central flow tube. Indeed, each of the cells 180 is tilted in the same direction. However, there are two rows of three cells 180 each stacked along the central axis 176 that are offset lengthwise from each other such that there are spaces in the struts on the opposite obtuse corners of the parallelogram 182. Specifically, as highlighted, a lower cell row 184a extends to the left end wall 172a but there is a space 186a between it and the right end wall 172b. Conversely, an upper cell row 184b extends to the right end wall 172b but defines a space 186b between it and the left end wall 172a. Consequently, the right end wall 172b directly connects only to the upper row 184b of cells while the left end wall 172a directly connects only with the lower row 184a of cells. These spaces facilitate collapse of the shunt 150 for delivery through the catheter as described herein.

FIG. 8A is a flattened view of the expandable shunt 150 as if a shunt had been severed along one of the end walls 172 and along the midline of the associated flanges 152, 154. This view illustrates orientations of the parallelogram-shaped cells 180 in the side walls 170 relative to parallelogram-shaped cells 188 in the end walls 172. Once again, the upper and lower cell rows 184a, 184b in one of the side walls 170 are highlighted. The parallelogram-shaped cells 180 in these rows are angled in one direction, in this case in a clockwise tilt. The adjacent cell 188 in the end wall 172 is on the other hand angled in the opposite direction, with a counterclockwise tilt. This is also seen clearly in the adjacent perspective view of FIG. 8D. This beneficial juxtaposition of the oppositely-tilted cells 180, 188 facilitates collapse of the shunt 150. That is, the super elastic material making up the struts easily flexes into an elongated shape, as will be seen below with respect to FIGS. 9A-9D.

FIGS. 8A-8C also shows several dimensions and a preferred configuration for the terminal ends 160, 164 of the flanges. In one embodiment, a spacing S across the struts that define the cells 180, 188 is between 1.5-2.5 mm, and preferably about 1.6 mm. The thickness t of the struts that define the cells 180, 188 is at least 0.2 mm, preferably between 0.2-0.3 mm. The terminal ends 164 of each proximal flange 154 defines a buckle 190, seen enlarged in FIG. 8B. The buckles 190 are provided on the terminal ends 164 of the proximal flanges 154 so that they may be engaged by the first and second actuating rods 162, as described above. Each buckle 190 desirably comprises a generally rectangular periphery with a rectangular aperture 192 therein. A width dimension $W_1$ of each buckle 190 is desirably between 2-3 mm, and preferably about 2.7 mm. FIG. 8B also shows slightly thicker struts 194 having a thickness dimension T of between 0.4-0.5 mm, which are utilized on the outer edges of the flanges 152, 154. The terminal ends 160 of the distal flanges 152, as seen in FIG. 8C, are shaped as elongated rectangles having rectangular cutouts 196 to reduce their stiffness. The apertures 192 in the buckles 190 also increase their flexibility, and the flexible terminal ends 160, 164 are therefore less traumatic to the tissue wall 30.

With respect to FIG. 8A, the different strut configuration of the flanges 152a, 154a are detailed. As seen in the partial perspective of FIG. 8D, the two opposed clamping flanges on each longitudinal side of the central flow tube 166 extend away in the same direction from the corresponding end wall 172a. FIG. 8A shows, however, that the proximal flange 154a, in this case the shorter flange, comprises both thin struts 179 and thick struts 194 that extend from the end wall 172a (or at least from a junction of the end wall 172a and side walls 170), whereas the longer distal flange 152a has thin struts 179 that connect to the end wall 172a and thick struts 194 that connect to the side walls 170. Conversely, the flanges 152b, 154b located 180° around the central flow tube 166 are configured similarly but the longer strut is on the proximal end while the shorter strut is on the distal end. On both ends it is the shorter strut that connects just to the end wall 172 and thus is more flexible. That is, the struts of the shorter proximal flange 154a converge toward each other at the end wall 172a, as seen in FIG. 8A, which reduces the lateral size of the hinge about which they pivot when they convert from their elongated state within the catheter to their bent shape when implanted. The longer distal flange 152a also rotates outward when released but not quite as far as the shorter flange. This difference in movement can best be seen in FIG. 10, and can be summarized by noting that when the shunt 150 expands, the shorter flanges rotate outward more than 90° while the longer flanges rotate less than 90°.

It should be understood that the various struts that form the shunt 150 are desirably fabricated by laser cutting a Nitinol tube. The tube desirably has a wall thickness of between about 0.1-0.3 mm, and preferably about 0.2 mm. A preferred method for cutting the shape of the shunt 150 will become clearer below with respect to the collapsed views of FIGS. 9A-9D.

FIGS. 9A-9D are perspective and orthogonal views of the exemplary expandable shunt 150 in a collapsed configuration for delivery through an access sheath or catheter. In this configuration, the shunt 150 describes a tubular form. That is, the flanges 152, 154 form extensions of the end walls 172, and together with the side walls 170 form a tube. Indeed, this is the shape that the shunt 150 has immediately after being laser cut from a tubular workpiece. The laser passes across the tube at an angle parallel to the reference plane P shown in FIG. 9B. Moreover, the laser is programmed to move along a flat pattern such as shown in FIG. 8A wrapped around the tube. The resulting tubular form of the shunt 150 may then be deformed using mandrels and the like to bend the flanges 152, 154 outward into the configuration shown, for example, in FIGS. 6A and 6B. The shunt 150 in its deformed shape is then heat treated such that the Nitinol material reaches a transition temperature and the expanded shape becomes the relaxed shape. However, the Nitinol can then be easily reformed by bending into the tubular shape of FIGS. 9A-9D for loading within the delivery catheter.

FIG. 10 is a schematic view of a delivery catheter such as that shown at 50 in FIGS. 3N-3T passing at an angle through a tissue wall 30 with the exemplary expandable shunt 150 therein in a collapsed configuration, as was shown in FIGS. 9A-9D. The shunt 150 is also shown in phantom as it would be expanded in contact with the tissue wall 30. This clearly illustrates the advantageous tilted configuration of the struts and cells of the side walls 170 of the shunt 150 which are oriented along angled axis 176. The axis 176 coincides with the longitudinal axis of the delivery catheter 50, which passes through a puncture hole angled in the same direction through the tissue wall 30. In this way, the shunt 150 can be implanted in the tissue wall 30 using a catheter 50 that passes through at an angle. Once expanded, as seen in dashed line, the flanges 152, 154 clamp about the tissue wall 30 and maintain the central flow tube 166 within the puncture wound. Furthermore, as mentioned above, when the shunt 150 expands, the shorter flanges (154a, 152b) bend outward more than 90° while the longer flanges (152a, 154b) bend less than 90°.

Figure 11A:
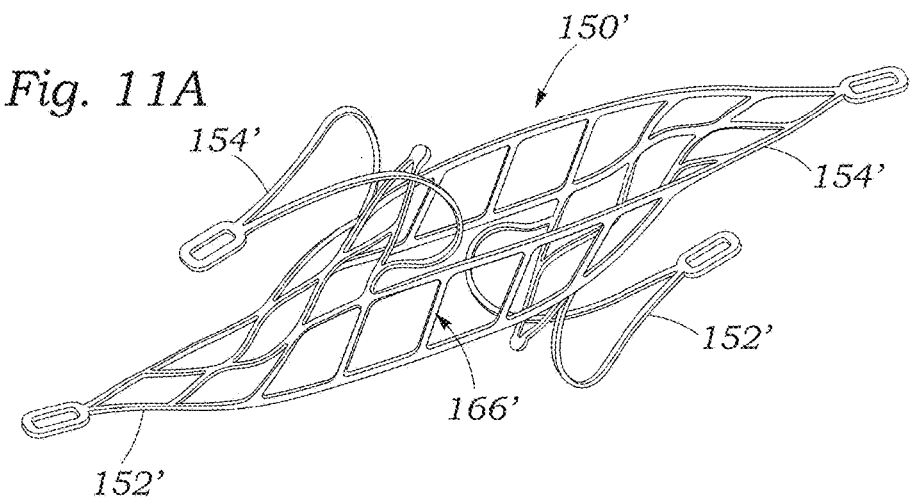
FIGS. 11A-11C are perspective and elevational views of an alternative expandable shunt of the present application.
Figure 11B:
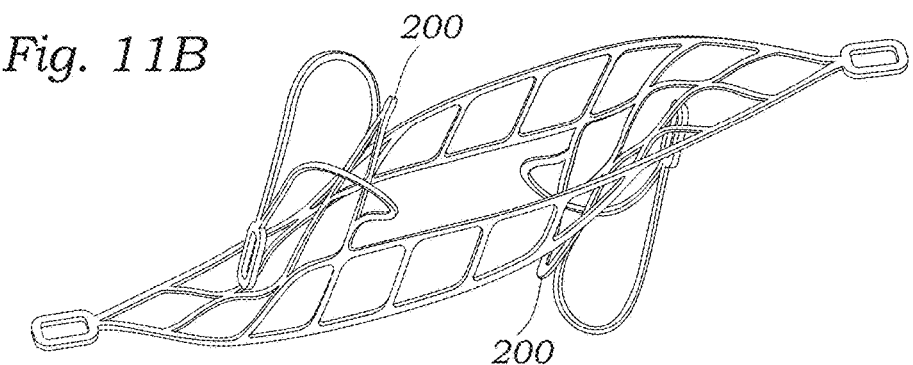
Figure 11C:
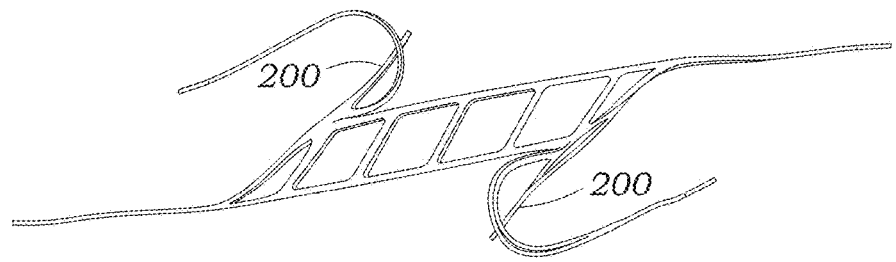

FIGS. 11A-11C are perspective and elevational views of an alternative expandable shunt 150' of the present application. This configuration also features distal and proximal flanges 152', 154', and a central flow tube 166'. The flow tube 166' is somewhat shallower than the first embodiment, and the flanges 152', 154' have slightly different shapes, but the overall configuration is similar and again facilitates collapse into the catheter 142. One primary difference is the provision of fingers 180 on either end wall of the central flow tube 166' extending in opposite directions that help define and maintain open the blood flow path.

FIGS. 12 and 12A-12C are a number of views of an exemplary puncture catheter 222 having a side-extending needle used to create a puncture in a sidewall of a vessel, much as described above with respect to the puncture catheter 22 of FIGS. 3A-3L. The puncture catheter includes an elongated, flexible hollow sheath 221 that extends to a curved distal portion terminating in an extreme distal segment 225. The curved distal portion is shown enlarged in FIG. 12A, and includes an expandable anchoring member 224 on an outer radial side opposite a side-extending puncture sheath 232 having a sharp puncture needle 234. The puncture sheath 232 projects through a side port (not shown) on an inner radial side. As explained above, the puncture needle 232 comprises an elongated flexible or wire having a sharp distal tip. A pair of radiopaque markers 226 flank the anchoring member 224 and locate the side port from which the puncture sheath 232 emerges.

FIG. 13 is a vertical sectional view through a proximal handle 240 of the puncture catheter 222 of FIG. 12C. The hollow sheath 221 of the puncture catheter 222 defines several internal pathways or lumens (not numbered) for at least the elongated puncture sheath 232 and a guidewire 220 (such as guide wire 20 in FIG. 3A). The proximal handle 240 defines Y-shaped internal channels such that the puncture sheath 232 continues straight out of the hollow sheath 221 and to a pusher or advancer 242, while the guidewire 220 passes through a divergent port which leads to a proximal luer fitting 244. The luer fitting 244 provides means for flushing the entire guidewire channel/lumen. The puncture sheath 232 is fixed within the needle advancer 242 which is arranged to slide in a proximal-distal direction through a rear bracket 246. When the needle advancer 242 is displaced distally, the puncture sheath 232 slides through a locking nut 248 that is fixed with respect to a forward bracket 249. The locking nut 248 enables the advancer 242 and puncture sheath 232 to be fixed relative to the handle 240. In this way, the physician can project or retract the puncture sheath 232 from the side opening of the catheter 222, and fix its position in either location.

An inner needle 235 passes through the puncture sheath 232 and terminates in the sharp puncture needle 234. As seen in FIG. 13, the inner needle 235 extends from the rear of the puncture sheath 232 and is fixed within a hollow fitting 236. The hollow fitting 236, in turn, fits closely and is sealed within a proximal junction 243 on the advancer 242. By pulling out the hollow fitting 236, the inner needle 235 may be retracted into and then removed from the puncture sheath 232 after forming the puncture. This leaves the lumen of the puncture sheath 232 open for passage of the second guidewire 36 (see FIG. 3F) that enters the left atrium. Also, the puncture sheath 232 may be removed completely and replaced with the puncture expander 40 used to widen the puncture between the coronary sinus and left atrium, as seen in FIGS. 3H-3J.

FIG. 14A is an elevational view of a shunt deployment catheter 250 of the present application showing interior components of a proximal handle 264, and FIG. 14B is an enlarged view of a distal end thereof having a soft curved distal tip 252. As described above, the expandable shunt 150 is carried on an inner sheath 256 over which concentrically slides an outer sheath 260. The shunt 150 collapses down primarily within a pair of opposed side recesses or openings 262 so that the sheath 260 can slide over it and maintain it in its collapsed configuration. The shunt 150 mounts in its collapsed configuration with its central axis 176 (see FIG. 6C) therethrough coinciding with a longitudinal axis of the inner sheath 256 at the recesses 262.

The outer sheath 260 passes into the proximal handle 264, and the inner sheath 256 continues and is fixed therein. A sliding mechanism 266 surrounds and fastens to the outer sheath 260, and initiates axial movement relative to the inner sheath 256. A pair of flexible arms 268 project from a rear end of the handle 264 and connect to a pair of actuating rods (such as actuating rods 162a, 162b shown in FIGS. 4A-4H) that extend through the inner sheath 2564 manipulation of the expandable shunt 150. Controlled release of the shunt 150 may thus be done manually by the physician, or the actuating rods may be attached to separate sliders on the handle 264.

FIG. 14B shows the end of the deployment catheter 250 after the sheath 260 retracts. Initially, the shunt 150 is compressed down to its generally tubular configuration and held in the annular space between the inner sheath 256 and outer sheath 260. The side openings 262 provide recesses for the shunt flanges 152, 154, as well as a portion of the actuating rods 162a, 162b, to lie against the inner sheath 256. When the outer sheath 260 retracts the central flow tube 166 of the shunt 150 expands and the flanges 152, 154 are permitted to expand, though the proximal flange are controlled by the actuating rods 162a, 162b.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A system for deploying an expandable shunt into a puncture wound in a tissue wall to maintain an opening therebetween, the wall defining a reference plane, comprising:
the expandable shunt comprising, in an expanded state:
a central flow tube defining a central axis therethrough;
distal flanges attached to a first axial end of the central flow tube; and
proximal flanges attached to a second axial end of the central flow tube opposite the first end;
a delivery catheter having a proximal handle, an outer sheath surrounding an inner sheath, the shunt being mounted in a collapsed configuration on the inner sheath with the outer sheath surrounding and maintaining the shunt in a collapsed state with the proximal flanges oriented toward the handle, and a pair of actuating rods extending from the handle distally through the inner sheath each of which engages one of the proximal flanges of the shunt, the actuating rods being linearly slidable within the inner sheath;
a puncture catheter having a proximal handle, an elongated flexible body having a distal tip, a guidewire lumen extending through the body from the handle to the distal tip, and a needle lumen extending through the body from the handle to a side port located near the distal tip; and
an elongated puncture sheath having a lumen and an elongated needle having a sharp tip sized to fit through the puncture sheath lumen such that the sharp tip projects therefrom, the puncture sheath being sized to pass through the needle lumen of the puncture catheter and project out of the side port to form a puncture in a tissue wall.

2. The system of claim 1, further including an expandable member sized to pass through the needle lumen and project out of the side port into the puncture, the expandable member being radially expandable to widen the puncture.

3. The system of claim 1, wherein in the shunt there are two distal flanges formed by struts and extending away from one another in opposite longitudinal directions, and there are two proximal flanges formed by struts and extending away from one another in opposite longitudinal directions and in the same directions as the distal flanges, wherein each proximal flange parallels one of the distal flanges to form a clamping pair of flanges with a gap therebetween sized to clamp onto the tissue wall.

4. The system of claim 3, wherein each clamping pair of flanges includes flanges of different lengths.

5. The system of claim 3, wherein when the shunt expands a first flange in each clamping pair of flanges rotates outward more than 90° and a second flange in the same clamping pair of flanges rotates outward less than 90°.

6. The system of claim 1, wherein in the shunt the central flow tube is defined by an opposed pair of lateral side walls formed by struts extending between an opposed pair of end walls formed by struts, the central flow tube defining a central axis therethrough angled from a reference axis extending perpendicular through the reference plane.

7. The system of claim 5, wherein the shunt is mounted in its collapsed configuration within a recess near a distal end of the inner sheath with the central axis therethrough coinciding with a longitudinal axis of the inner sheath at the recess.

8. The system of claim 1, further including an expandable anchoring member located on the flexible body opposite the side port.

9. The system of claim 8, further including a pair of radiopaque markers located distal and proximal to the expandable anchoring member on the side port side of the flexible body.

10. The system of claim 1, wherein the puncture catheter proximal handle includes an advancer for displacing the puncture sheath and a locking nut that fixes the puncture sheath relative to the handle.

11. A system for deploying an expandable shunt into a puncture wound in a tissue wall to maintain an opening therebetween, the wall defining a reference plane, comprising:
the expandable shunt comprising, in an expanded state:
a central flow tube defining a central axis therethrough;
distal flanges attached to a first axial end of the central flow tube; and
proximal flanges attached to a second axial end of the central flow tube opposite the first end;
a delivery catheter having a proximal handle, an outer sheath surrounding an inner sheath, the shunt being mounted in a collapsed configuration on the inner sheath with the outer sheath surrounding and maintaining the shunt in a collapsed state with the proximal flanges oriented toward the handle, and a pair of actuating rods extending from the handle distally through the inner sheath each of which engages one of the proximal flanges of the shunt, the actuating rods being linearly slidable within the inner sheath;
a puncture catheter having a proximal handle, an elongated flexible body having a distal tip, a guidewire lumen extending through the body from the handle to the distal tip, and a needle lumen extending through the body from the handle to a side port located near the distal tip, the puncture catheter further including an expandable anchoring member located on the flexible body opposite the side port; and
an elongated puncture sheath sized to pass through the needle lumen of the puncture catheter and project out of the side port to form a puncture in a tissue wall.

12. The system of claim 11, wherein the elongated puncture sheath has a lumen and an elongated needle having a sharp tip sized to fit through the puncture sheath lumen such that the sharp tip projects therefrom.

13. The system of claim 11, further including an expandable member sized to pass through the needle lumen and project out of the side port into the puncture, the expandable member being radially expandable to widen the puncture.

14. The system of claim 11, wherein in the shunt there are two distal flanges formed by struts and extending away from one another in opposite longitudinal directions, and there are two proximal flanges formed by struts and extending away from one another in opposite longitudinal directions and in the same directions as the distal flanges, wherein each proximal flange parallels one of the distal flanges to form a clamping pair of flanges with a gap therebetween sized to clamp onto the tissue wall.

15. The system of claim 13, wherein each clamping pair of flanges includes flanges of different lengths.

16. The system of claim 13, wherein when the shunt expands a first flange in each clamping pair of flanges rotates outward more than 90° and a second flange in the same clamping pair of flanges rotates outward less than 90°.

17. The system of claim 11, wherein in the shunt the central flow tube is defined by an opposed pair of lateral side walls formed by struts extending between an opposed pair of end walls formed by struts, the central flow tube defining a central axis therethrough angled from a reference axis extending perpendicular through the reference plane.

18. The system of claim 15, wherein the shunt is mounted in its collapsed configuration within a recess near a distal end of the inner sheath with the central axis therethrough coinciding with a longitudinal axis of the inner sheath at the recess.

19. The system of claim 11, further including a pair of radiopaque markers located distal and proximal to the expandable anchoring member on the side port side of the flexible body.

20. The system of claim 11, further including an elongated puncture sheath having a lumen and an elongated needle having a sharp tip sized to fit through the puncture sheath lumen such that the sharp tip projects therefrom, the puncture sheath being sized to pass through the needle lumen and project out of the side port to form a puncture in a tissue wall, wherein the puncture catheter proximal handle includes an advancer for displacing the puncture sheath and a locking nut that fixes the puncture sheath relative to the handle.

* * * * *